United States Patent
Christiansen et al.

(10) Patent No.: US 9,359,278 B2
(45) Date of Patent: Jun. 7, 2016

(54) ORGANOPHOSPHORUS COMPOUNDS BASED ON ANTHRACENETRIOL

(71) Applicants: Andrea Christiansen, Neu-Ulm (DE); Robert Franke, Marl (DE); Dirk Fridag, Haltern am See (DE); Dieter Hess, Marl (DE); Burkard Kreidler, Essen (DE); Detlef Selent, Rostock (DE); Armin Boerner, Rostock (DE)

(72) Inventors: Andrea Christiansen, Neu-Ulm (DE); Robert Franke, Marl (DE); Dirk Fridag, Haltern am See (DE); Dieter Hess, Marl (DE); Burkard Kreidler, Essen (DE); Detlef Selent, Rostock (DE); Armin Boerner, Rostock (DE)

(73) Assignee: EVONIK DEGUSSA GmbH, Essen (DE)

( * ) Notice: Subject to any disclaimer, the term of this patent is extended or adjusted under 35 U.S.C. 154(b) by 82 days.

(21) Appl. No.: 14/357,090

(22) PCT Filed: Oct. 24, 2012

(86) PCT No.: PCT/EP2012/071060
§ 371 (c)(1),
(2) Date: May 8, 2014

(87) PCT Pub. No.: WO2013/068232
PCT Pub. Date: May 16, 2013

(65) Prior Publication Data
US 2014/0309423 A1  Oct. 16, 2014

(30) Foreign Application Priority Data
Nov. 8, 2011 (DE) .......... 10 2011 085 883

(51) Int. Cl.
*C07F 15/00* (2006.01)
*C07F 9/655* (2006.01)
*C07C 45/50* (2006.01)
*C07F 9/6574* (2006.01)
*B01J 31/22* (2006.01)

(52) U.S. Cl.
CPC .......... *C07C 45/505* (2013.01); *B01J 31/2295* (2013.01); *C07C 45/50* (2013.01); *C07F 9/65746* (2013.01); *C07F 15/008* (2013.01); *C07F 15/0073* (2013.01)

(58) Field of Classification Search
USPC .............. 568/17, 12, 13; 252/182.18; 556/13
See application file for complete search history.

(56) References Cited

U.S. PATENT DOCUMENTS

| | | |
|---|---|---|
| 4,694,109 A | 9/1987 | Devon et al. |
| 4,851,581 A | 7/1989 | Devon et al. |
| 4,904,808 A | 2/1990 | Devon et al. |
| 5,817,848 A | 10/1998 | Kamer et al. |
| 7,009,068 B2 | 3/2006 | Schmutzler et al. |
| 7,161,020 B2 | 1/2007 | Selent et al. |
| 7,495,133 B2 | 2/2009 | Borgmann et al. |
| 7,767,861 B2 | 8/2010 | Ortmann et al. |
| 2009/0292146 A1 | 11/2009 | Hess et al. |
| 2010/0137623 A1 | 6/2010 | Selent et al. |
| 2012/0197025 A1 | 8/2012 | Christiansen et al. |
| 2013/0158282 A1 | 6/2013 | Christiansen et al. |

FOREIGN PATENT DOCUMENTS

| | | |
|---|---|---|
| FR | 2 215 221 A1 | 8/1974 |
| WO | WO 95/30680 A1 | 11/1995 |
| WO | WO 03/016320 A1 | 2/2003 |
| WO | WO 03/016321 A2 | 2/2003 |
| WO | WO 2005/063776 A1 | 7/2005 |
| WO | WO 2005/090276 A1 | 9/2005 |
| WO | WO 2008/012128 A1 | 1/2008 |
| WO | WO 2008/141853 A1 | 11/2008 |
| WO | WO 2011/023756 A2 | 3/2011 |
| WO | WO 2011/107441 A1 | 9/2011 |

OTHER PUBLICATIONS

International Search Report issued Nov. 30, 2012, in PCT/EP12/071060 filed Oct. 24, 2012.

*Primary Examiner* — Charanjit Aulakh
(74) *Attorney, Agent, or Firm* — Oblon, McClelland, Maier & Neustadt, L.L.P.

(57) ABSTRACT

The subject matter of the present invention is a plurality of products and the use thereof as a catalytically active composition in a method for producing aldehydes.

24 Claims, 1 Drawing Sheet

BiPhePhos

ORGANOPHOSPHORUS COMPOUNDS BASED ON ANTHRACENETRIOL

The present invention relates to bis- and trisphosphites containing at least one structural element based on anthracenetriol and also to metal complexes thereof, to the preparation, and also to the use of the bis- and trisphosphites as multidentate compounds in catalytic reactions.

The reactions between olefin compounds, carbon monoxide and hydrogen in the presence of a catalyst to form the aldehydes having one carbon atom more is known as hydroformylation (oxo synthesis). Catalysts used in these reactions are frequently compounds of the transition metals of group VIII of the periodic table, especially compounds of rhodium and of cobalt. Hydroformylation using rhodium compounds generally offers the advantage of higher selectivity compared with catalysis using cobalt and leads to products having a higher added value. Rhodium-catalyzed hydroformylation usually employs compositions that consist of rhodium and preferably of trivalent phosphorus compounds as ligands. Known ligands are for example compounds from the classes of phosphines, phosphites and phosphonites each comprising trivalent phosphorus $P^{III}$. Hydroformylation of olefins is reviewed in B. CORNILS, W. A. HERRMANN, "Applied Homogeneous Catalysis with Organometallic Compounds", Vol. 1 & 2, VCH, Weinheim, N.Y., 1996.

Every catalytically active composition—based on cobalt or rhodium—has its specific merits. Different catalytically active compositions are therefore used depending on the feedstock and the target product, as is shown by the following examples: With rhodium and triphenylphosphine, α-olefins can be hydroformylated at comparatively low pressures. Triphenylphosphine as phosphorus-containing ligand is generally used in excess, while a high ligand/rhodium ratio is required to increase the selectivity of the reaction leading to the commercially desired n-aldehyde product.

The U.S. Pat. No. 4,694,109 and U.S. Pat. No. 4,879,416 describe bisphosphine ligands and their use in the hydroformylation of olefins at low syngas pressures. Ligands of this type provide high activities and high n/i selectivities in the hydroformylation of propene in particular. WO 95/30680 discloses bidentate phosphine ligands and their use in catalysis including inter alia in hydroformylation reactions. Ferrocene-bridged bisphosphines are described for example in the U.S. Pat. No. 4,169,861, U.S. Pat. No. 4,201,714 and U.S. Pat. No. 4,193,943 as ligands for hydroformylations.

The disadvantage of bi- and polydentate phosphine ligands is their relatively costly and inconvenient method of making. Therefore, it is often not economically viable to use such systems in commercial processes. There is also the comparatively low reactivity, which has to be technically compensated by high residence times. This in turn leads to undesired secondary reactions for the products.

Rhodium-monophosphite complexes in catalytically active compositions are useful for the hydroformylation of branched olefins having internal double bonds, but selectivity is low in respect of terminally hydroformylated compounds. EP 0 155 508 discloses the use of bisarylene-substituted monophosphites in the rhodium-catalyzed hydroformylation of sterically hindered olefins, e.g. isobutene.

Catalytically active compositions based on rhodium-bisphosphite complexes are useful for the hydroformylation of linear olefins having terminal and internal double bonds to give predominantly terminally hydroformylated products. By contrast, branched olefins having internal double bonds are only converted to a minor extent. These phosphites coordinate onto a transition metal centre to provide catalysts of enhanced activity, but the on-stream life of these catalytically active compositions is unsatisfactory, inter alia because of the phosphite ligands' sensitivity to hydrolysis. The use of substituted bisaryl diols as starting materials for the phosphite ligands, as described in EP 0 214 622 or EP 0 472 071, wrought appreciable improvements.

The literature says that the catalytically active compositions of these ligands based on rhodium are extremely active in the hydroformylation of α-olefins. The U.S. Pat. No. 4,668,651, U.S. Pat. No. 4,748,261 and U.S. Pat. No. 4,885,401 describe polyphosphite ligands with which α-olefins but also 2-butene can be converted to the terminally hydroformylated products with high selectivity. Bidentate ligands of this type have also been used for hydroformylating butadiene (U.S. Pat. No. 5,312,996).

The bisphosphites disclosed in EP 1 294 731, when used in the hydroformylation of octene mixtures, provide olefin conversions of up to 98%. However, the likewise desired n-selectivity to nonanal at 36.8% to at most 57.6% is in need of improvement. This applies all the more because the use of a catalytically active composition in commercial processes requires an on-stream life of days rather than hours.

Although the bisphosphites mentioned are good ligands for rhodium-based hydroformylation catalysts, it is desirable to develop novel ligands.

These novel ligands shall:

have high n-selectivities in the hydroformylation of olefins or olefin-containing mixtures with internal double bonds, i.e. isomerizing properties;

also possess an improved resistance to inherent catalyst poisons, such as water for example, and thus provide prolonged on-stream life when used in a catalytically active composition for hydroformylation;

and also reduce the known clustering tendency of rhodium in catalytically active compositions and thereby again provide prolonged on-stream life when used in a catalytically active composition for hydroformylation.

This object is achieved by a compound according to the present invention comprising the structural element (I):

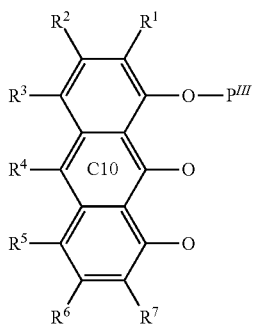

(I)

and
the compound comprises at least two O—P$^{III}$ bonds, wherein these may emanate from the same P$^{III}$ or from different P$^{III}$s;
in the event that the structural element (I) occurs twice in the compound, these are connected to each other by a C10-C10' carbon bond or via the following X$^1$-G$^1$-X$^2$ unit:

—X$^1$-G$^1$-X$^2$— where X$^1$ is connected to a P$^{III}$ of the first structural element (I) and X$^2$ to a P$^{III}$ of the second structural element (I), with G$^1$=a linear or branched, aliphatic or aromatic or heteroaromatic or fused aromatic or fused aromatic-heteroaromatic hydrocarbon group with any desired further substitution;
wherein X$^1$, X$^2$ is selected from: O, NY$^1$, CY$^2$Y$^3$;
wherein the meaning may have been chosen for X$^1$ and X$^2$ independently of each other;
wherein Y$^1$, Y$^2$, Y$^3$ is selected from: hydrogen, substituted or unsubstituted aliphatic, substituted or unsubstituted aromatic hydrocarbon group;
wherein the meaning may have been chosen for each Y$^1$ to Y$^3$ independently of each other;
wherein two or more of Y$^1$ to Y$^3$ may be linked to each other covalently;
wherein R$^1$, R$^2$, R$^3$, R$^4$, R$^5$, R$^6$, R$^7$ are selected from: hydrogen, substituted or unsubstituted, linear or branched, aliphatic or aromatic hydrocarbon group; F, Cl, Br, I, —OR$^8$, —C(O)R$^9$, —CO$_2$R$^{10}$, —CO$_2$M$^1$, —SR$^{11}$, —SOR$^{12}$, —SO$_2$R$^{13}$, —SO$_3$R$^{14}$, —SO$_3$M$^2$, —NR$^{15}$R$^{16}$;
wherein R$^8$, R$^9$, R$^{10}$, R$^{11}$, R$^{12}$, R$^{13}$, R$^{14}$, R$^{15}$, R$^{16}$ are selected from: hydrogen, substituted or unsubstituted, linear or branched, aliphatic or aromatic or heteroaromatic or fused aromatic or fused aromatic-heteroaromatic hydrocarbon group; —OR$^{17}$;
wherein R$^{17}$ is selected from: hydrogen, unsubstituted or substituted, linear or branched, aliphatic or aromatic hydrocarbon group; wherein two or more of R$^1$ to R$^{17}$ may be linked to each other covalently;
wherein M$^1$ and M$^2$ are selected from: alkali metal, alkaline earth metal, ammonium, phosphonium, and wherein the meaning may have been chosen for M$^1$ and M$^2$ independently of each other.

In an embodiment of the invention, the compound comprises the structural element (II):

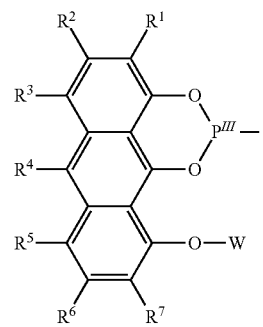

(II)

wherein W is selected from:
hydrogen;
aliphatic, aromatic, heteroaromatic, fused aromatic, fused aromatic-heteroaromatic hydrocarbon group with any desired further substitution;
a P$^{III}$(G$^2$)(G$^3$) group:

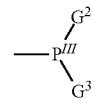

wherein G$^2$ and G$^3$ are each selected from: hydrogen; linear or branched, aliphatic or aromatic or heteroaromatic or fused aromatic or fused aromatic-heteroaromatic hydrocarbon group with any desired further substitution; F, Cl, Br, I, or —OR$^{18}$, —C(O)R$^{19}$, —CO$_2$R$^{20}$, —CO$_2$M$^1$, —SR$^{21}$, SOR$^{22}$, —SO$_2$R$^{23}$, —SO$_3$R$^{24}$, —SO$_3$M$^2$, —NR$^{25}$R$^{26}$;
wherein R$^{18}$, R$^{19}$, R$^{20}$, R$^{21}$, R$^{22}$, R$^{23}$, R$^{24}$, R$^{25}$, R$^{26}$ are selected from: hydrogen, substituted or unsubstituted, linear or branched, aliphatic or aromatic hydrocarbon group; —OR$^{27}$; wherein R$^{27}$ is selected from: hydrogen, substituted or unsubstituted, linear or branched, aliphatic or aromatic hydrocarbon group; F, Cl, Br, I;
wherein M$^1$ and M$^2$ are selected from: alkali metal, alkaline earth metal, ammonium, phosphonium, and
wherein the meaning may have been chosen for M$^1$ and M$^2$ independently of each other,
wherein the meaning may have been chosen for G$^2$ and G$^3$ independently of each other, and G$^2$ and G$^3$ may be linked to each other covalently,
—SiR$^{28}$R$^{29}$R$^{30}$; with R$^{28}$, R$^{29}$, R$^{30}$=hydrogen; linear or branched, aliphatic or aromatic or heteroaromatic or fused aromatic or fused aromatic-heteroaromatic hydrocarbon group with any desired further substitution; wherein the meaning may have been chosen for R$^{28}$, R$^{29}$ and R$^{30}$ independently of each other and wherein R$^{28}$ and R$^{29}$ may be linked to each other covalently.

In an embodiment of the invention, the compound comprises the structural element (III):

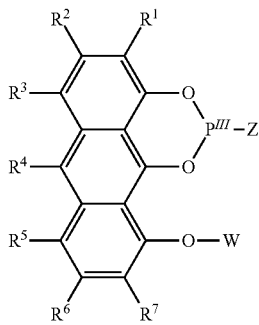

(III)

wherein Z represents $G^4$ or an $X^1$-$G^1$-$X^2$ unit,
and $G^4$ is selected from: hydrogen; linear or branched, aliphatic or aromatic or heteroaromatic or fused aromatic or fused aromatic-heteroaromatic hydrocarbon group with any desired further substitution; F, Cl, Br, I, or —$OR^{31}$, —C(O)$R^{32}$, —$CO_2R^{33}$, —$CO_2M^1$, —$SR^{34}$, —$SOR^{35}$, —$SO_2R^{36}$, —$SO_3R^{37}$, —$SO_3M^2$, —$NR^{38}R^{39}$,
wherein $R^{31}$, $R^{32}$, $R^{33}$, $R^{34}$, $R^{35}$, $R^{36}$, $R^{37}$, $R^{38}$, $R^{39}$ are selected from: hydrogen, substituted or unsubstituted, linear or branched, aliphatic or aromatic hydrocarbon group; —$OR^{40}$;
wherein $R^{40}$ is selected from: hydrogen, substituted or unsubstituted, linear or branched, aliphatic or aromatic hydrocarbon group;
wherein $M^1$ and $M^2$ are selected from: alkali metal, alkaline earth metal, ammonium, phosphonium, and
wherein the meaning may have been chosen for $M^1$ and $M^2$ independently of each other.

In an embodiment of the invention, the compound comprises the structural element (IV):

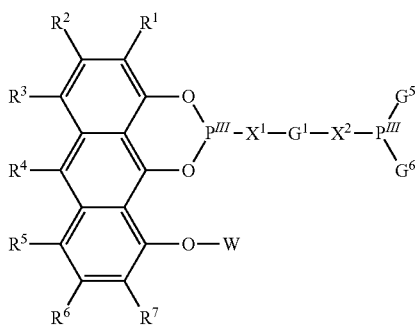

(IV)

wherein $G^5$ and $G^6$ are selected from: hydrogen; linear or branched; aliphatic or aromatic or heteroaromatic or fused aromatic or fused aromatic-heteroaromatic hydrocarbon group with any desired further substitution; F, Cl, Br, I, or —$OR^{41}$, —C(O)$R^{42}$, —$CO_2R^{43}$, —$CO_2M^1$, —$SR^{44}$, —$SOR^{45}$, —$SO_2R^{46}$, —$SO_3R^{47}$, —$SO_3M^2$, —$NR^{48}R^{49}$, wherein $R^{41}$, $R^{42}$, $R^{43}$, $R^{44}$, $R^{45}$, $R^{46}$, $R^{47}$, $R^{48}$, $R^{49}$ are selected from: hydrogen, substituted or unsubstituted, linear or branched, aliphatic or aromatic hydrocarbon group; —$OR^{50}$;
wherein $R^{50}$ is selected from: hydrogen, substituted or unsubstituted, linear or branched, aliphatic or aromatic hydrocarbon group;
wherein $M^1$ and $M^2$ are selected from: alkali metal, alkaline earth metal, ammonium, phosphonium, and
wherein the meaning may have been chosen for $M^1$ and $M^2$ independently of each other,
wherein the meaning may have been chosen for $G^5$ and $G^6$ independently of each other, and $G^5$ and $G^6$ may be linked to each other covalently.

In an embodiment of the invention, W represents a $P^{III}(G^2)(G^3)$ group.
In an embodiment of the invention, $G^2$, $G^3$ is =—$OR^{18}$.
In an embodiment of the invention, $G^5$, $G^6$ is =—$OR^{41}$.
In an embodiment of the invention, $X^1$, $X^2$ is =O.
In an embodiment of the invention, $G^1$ comprises a bisarylene group having any desired further substitution.
In an embodiment of the invention, $G^1$ comprises the structural element (V):

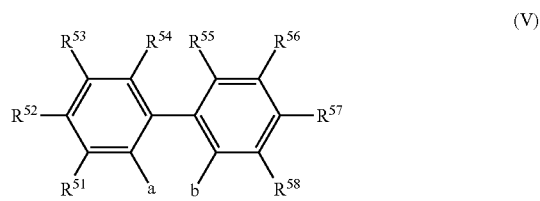

(V)

with $R^{51}$, $R^{52}$, $R^{53}$, $R^{54}$, $R^{55}$, $R^{56}$, $R^{57}$, $R^{58}$=hydrogen; linear or branched, aliphatic or aromatic or heteroaromatic or fused aromatic or fused aromatic-heteroaromatic hydrocarbon group with any desired further substitution; F, Cl, Br, or I; or —$OR^{59}$, —$COR^{60}$, —$CO_2R^{61}$, —$CO_2M^1$, —$SR^{62}$, —$SOR^{63}$, —$SO_2R^{64}$, —$SO_3R^{65}$, —$SO_3M^2$, —$NR^{66}R^{67}$, or N=$CR^{68}R^{69}$;
wherein the meaning may have been chosen independently for each $R^{51}$ to $R^{58}$ independently of each other and wherein two or more of $R^{51}$ to $R^{58}$ may be linked to each other covalently;
wherein $R^{59}$, $R^{60}$, $R^{61}$, $R^{62}$, $R^{63}$, $R^{64}$, $R^{65}$, $R^{66}$, $R^{67}$ are selected from: hydrogen, substituted or unsubstituted, linear or branched, aliphatic or aromatic hydrocarbon group; —$OR^{68}$;
wherein $R^{68}$ is selected from: hydrogen, substituted or unsubstituted, linear or branched, aliphatic or aromatic hydrocarbon group;
wherein $M^1$ and $M^2$ are selected from: alkali metal, alkaline earth metal, ammonium, phosphonium, and
wherein the meaning may have been chosen for $M^1$ and $M^2$ independently of each other,
and with a and b as attachment points to $X^1$ and $X^2$.

In an embodiment of the invention, $G^2$ and $G^3$ are linked to each other covalently.

In an embodiment of the invention, the link $G^2$-$G^3$ comprises the following structural element (VI):

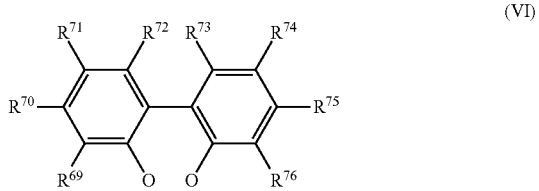

(VI)

with $R^{69}$, $R^{70}$, $R^{71}$, $R^{72}$, $R^{73}$, $R^{74}$, $R^{75}$, $R^{76}$=hydrogen; linear or branched, aliphatic or aromatic or heteroaromatic or fused aromatic or fused aromatic-heteroaromatic hydrocarbon group with any desired further substitution; F, Cl, Br, or I; or —$OR^{77}$, —$COR^{78}$, —$CO_2R^{79}$, —$CO_2M^1$, —$SR^{80}$, —$SOR^{81}$, —$SO_2R^{82}$, —$SO_3R^{83}$, —$SO_3M^2$, —$NR^{84}R^{85}$, or $N=CR^{86}R^{87}$; wherein the meaning may have been chosen for each $R^{69}$ to $R^{76}$ independently of each other and wherein two or more of $R^{69}$ to $R^{76}$ may be linked to each other covalently;

wherein $R^{77}$, $R^{78}$, $R^{79}$, $R^{80}$, $R^{81}$, $R^{82}$, $R^{83}$, $R^{84}$, $R^{85}$ are selected from: hydrogen, substituted or unsubstituted, linear or branched, aliphatic or aromatic hydrocarbon group; —$OR^{86}$;

wherein $R^{86}$ is selected from: hydrogen, substituted or unsubstituted, linear or branched, aliphatic or aromatic hydrocarbon group;

wherein $M^1$ and $M^2$ are selected from: alkali metal, alkaline earth metal, ammonium, phosphonium, and wherein the meaning may have been chosen for $M^1$ and $M^2$ independently of each other.

In an embodiment of the invention, $G^5$ and $G^6$ are linked to each other covalently.

In an embodiment of the invention, the link $G^5$-$G^6$ comprises the following structural element (VII):

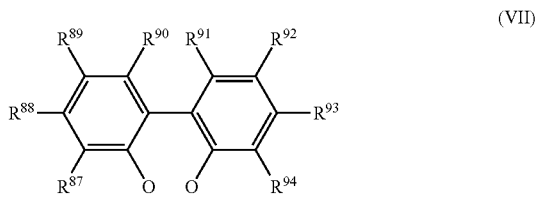

(VII)

with $R^{87}$, $R^{88}$, $R^{89}$, $R^{90}$, $R^{91}$, $R^{92}$, $R^{93}$, $R^{94}$=hydrogen; linear or branched, aliphatic or aromatic or heteroaromatic or fused aromatic or fused aromatic-heteroaromatic hydrocarbon group with any desired further substitution; F, Cl, Br, or I; or —$OR^{95}$, —$COR^{96}$, —$CO_2R^{97}$, —$CO_2M^1$, —$SR^{98}$, —$SOR^{99}$, —$SO_2R^{100}$, —$SO_3R^{101}$, —$SO_3M^2$, —$NR^{102}R^{103}$, or $N=CR^{104}R^{105}$; wherein the meaning may have been chosen for each $R^{31}$ to $R^{38}$ independently of each other and wherein two or more of $R^{86}$ to $R^{93}$ may be linked to each other covalently;

wherein $R^{95}$, $R^{96}$, $R^{97}$, $R^{98}$, $R^{99}$, $R^{100}$, $R^{101}$, $R^{102}$, $R^{103}$ are selected from: hydrogen, substituted or unsubstituted, linear or branched, aliphatic or aromatic hydrocarbon group; —$OR^{104}$;

wherein $R^{104}$ is selected from: hydrogen, substituted or unsubstituted, linear or branched, aliphatic or aromatic hydrocarbon group; wherein $M^1$ and $M^2$ are selected from: alkali metal, alkaline earth metal, ammonium, phosphonium, and wherein the meaning may have been chosen for $M^1$ and $M^2$ independently of each other.

In an embodiment of the invention, the $P^{III}(G^2)(G^3)$ group corresponds in terms of structural formula to the $P^{III}(G^5)(G^6)$ group.

In addition to the compound per se, complexes comprising such a compound are also claimed.

In an embodiment of the invention, the complex comprises a compound as described above and at least one central metal atom, wherein the compound is coordinated onto the central metal atom via at least one $P^{III}$.

In an embodiment of the invention, the central metal atom is selected from groups 8 to 10 of the periodic table of the elements.

In a preferred embodiment of the invention, the central metal atom is rhodium.

In addition to the complex itself, a composition comprising such a complex is also claimed.

In an embodiment, the composition contains a compound as described above which is not coordinated onto a central metal atom, and a complex as described above.

In addition to the composition, use thereof is also claimed.

In an embodiment, the composition is used as catalytically active composition in the synthesis of organic compounds.

In an embodiment, the composition is used as a catalytically active composition in a process for hydroformylation of olefinically unsaturated hydrocarbon mixtures.

A multiphasic reaction mixture is also claimed.

In an embodiment, the multiphasic reaction mixture contains an olefinically unsaturated hydrocarbon mixture, a gas mixture containing carbon monoxide and hydrogen, aldehydes, a composition as described above as catalytically active composition.

A process for hydroformylation of olefinically unsaturated hydrocarbon mixtures to aldehydes is also claimed.

In one version, this process comprises the steps of:
a) providing a mixture of olefinically unsaturated hydrocarbons;
b) adding a catalytically active composition as described above;
c) introducing a mixture comprising carbon monoxide and hydrogen;
d) heating the reaction mixture to a temperature in the range from 80 to 120° C.;
e) building a pressure in the range from 1.0 to 6.4 MPa;
f) removing the olefinically unsaturated hydrocarbon mixture on concluding the reaction.

In one version of the process, this process comprises as an additional step:

g) removing and returning unconverted olefinically unsaturated hydrocarbon mixture into step a).

In one version of the process, this process comprises as additional step:

h) removing and returning the catalytically active composition described to step b).

In one version of the process, this process comprises as additional step:

i) removing and returning the unconverted gas mixture containing carbon monoxide and hydrogen into step c).

Figure 1A:
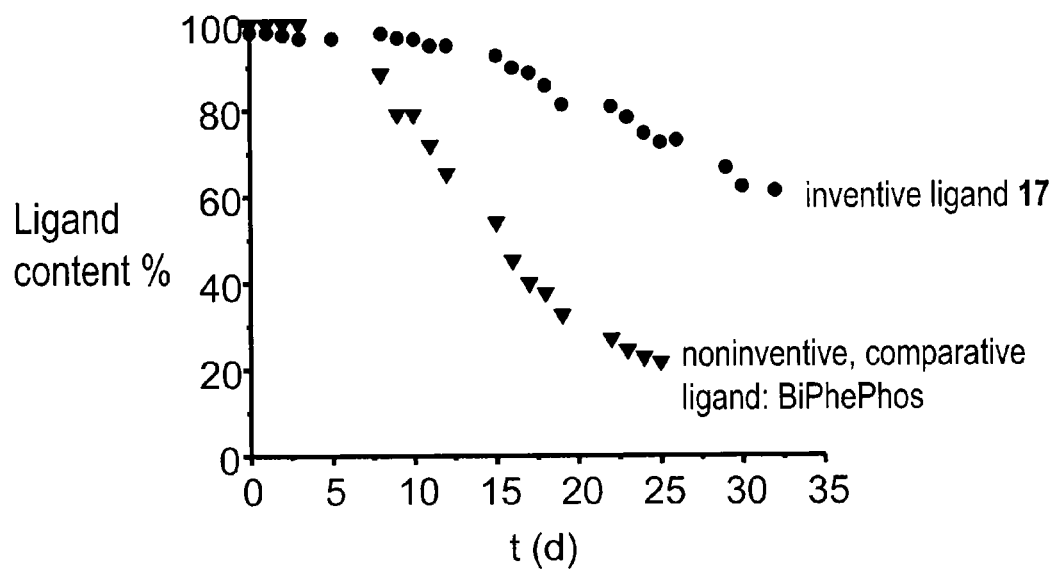
FIG. 1A. Comparison of % Ligand Content between comparative BiPhePhos ligand shown in FIG. 1B and Ligand 17. Ligand 17 has a significantly higher stability than the comparative ligand BiPhePhos which is no longer NMR-detectable after day 32. In comparison, the % ligand content of ligand 17 was measured at a concentration of 60% relative to its initial value.

Illustrative embodiments of compounds according to the present invention will now be shown: Illustrative embodiments of bidentate compounds according to the present invention with two phosphorus atoms:

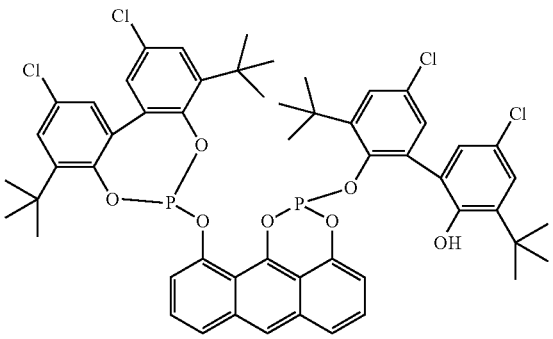

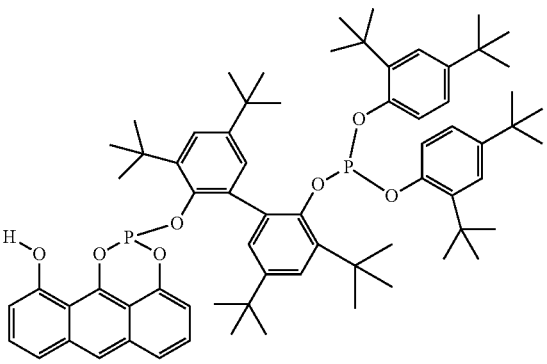

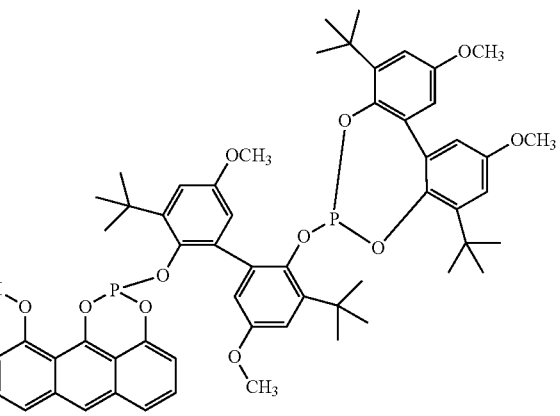

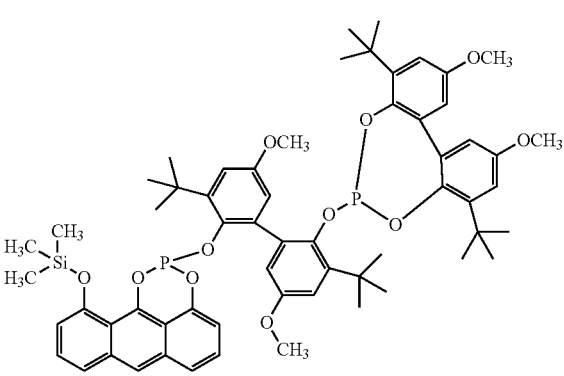

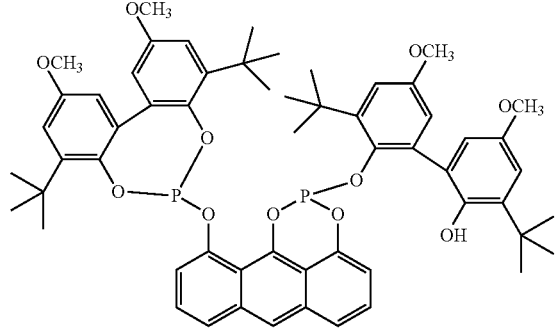

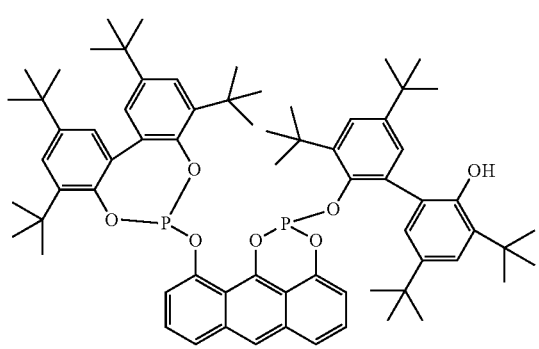

Illustrative embodiments of tridentate compounds according to the present invention with three phosphorus atoms:

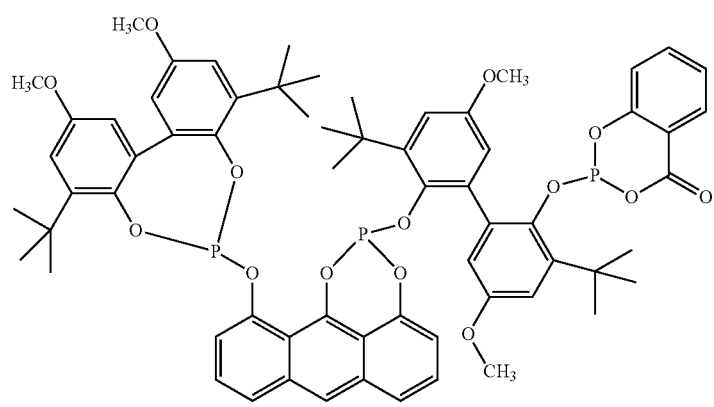
7
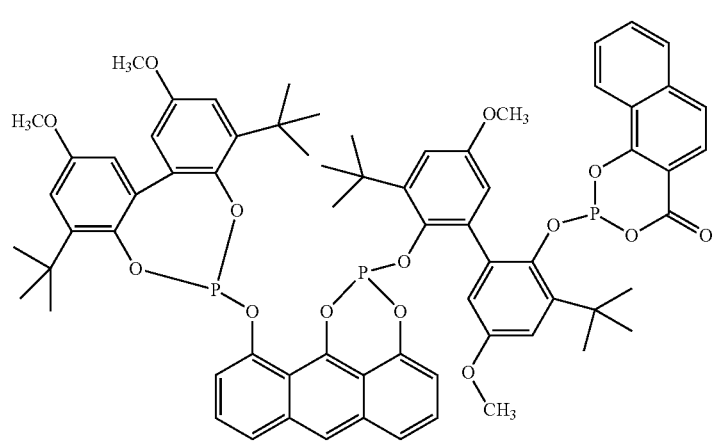
8
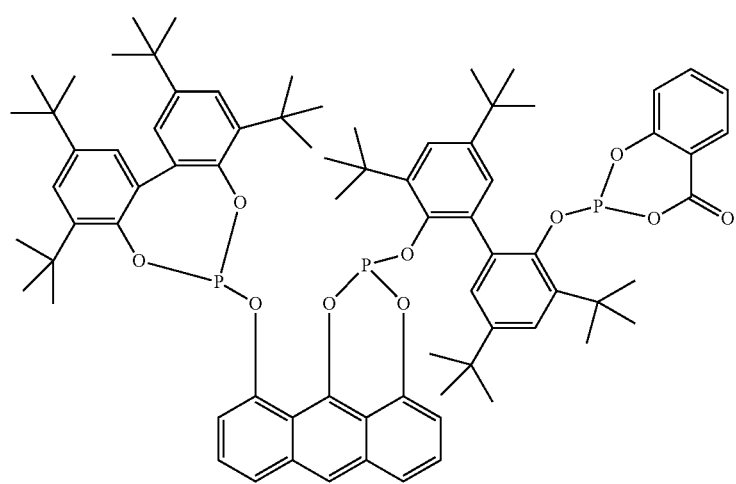
9

-continued
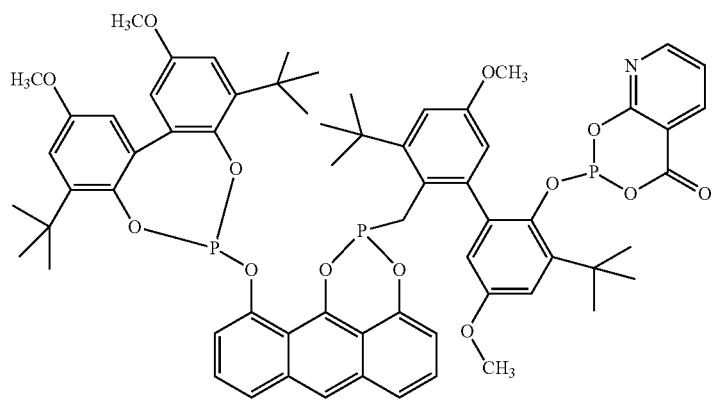
10
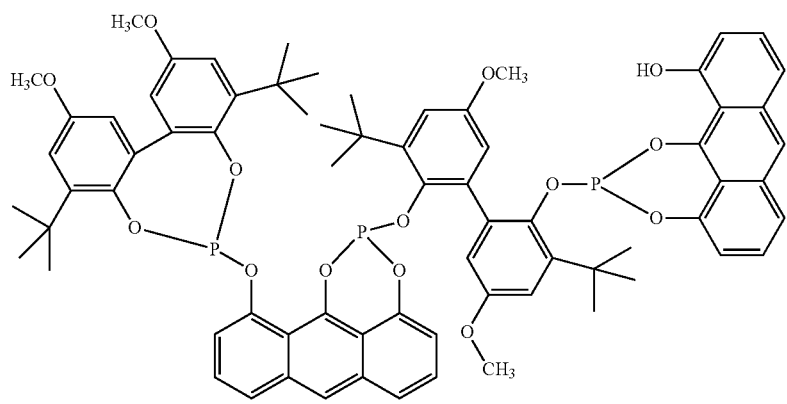
11
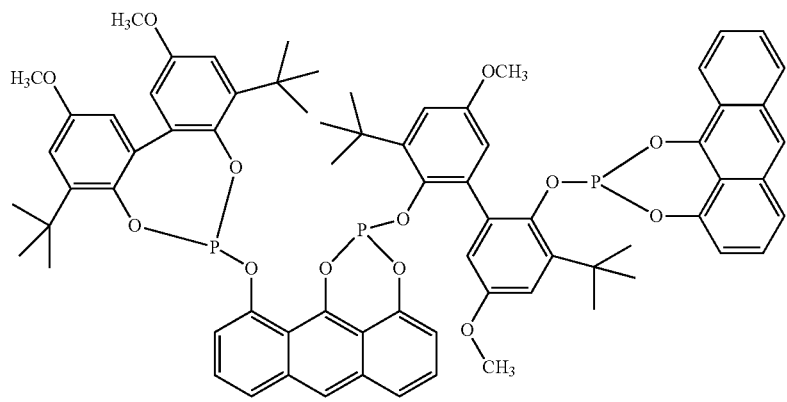
12

-continued
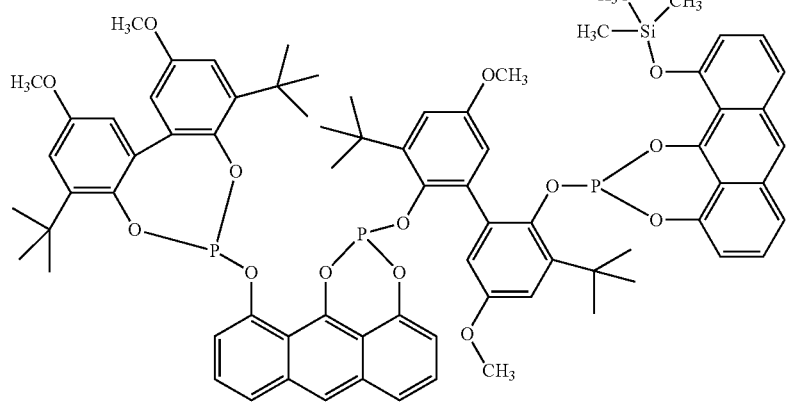
13
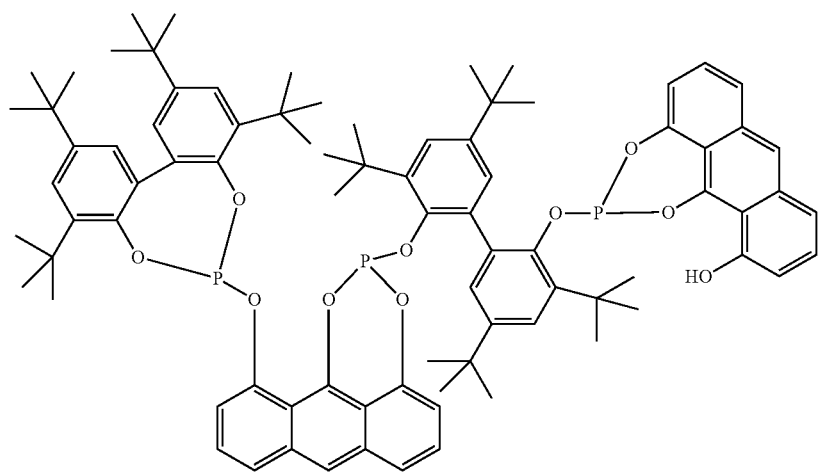
14
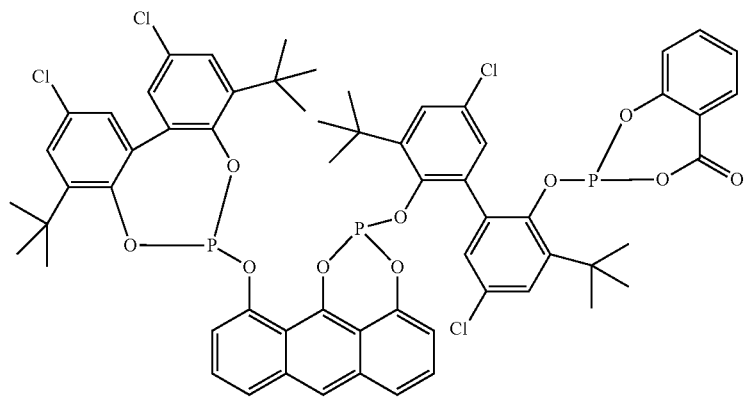
15

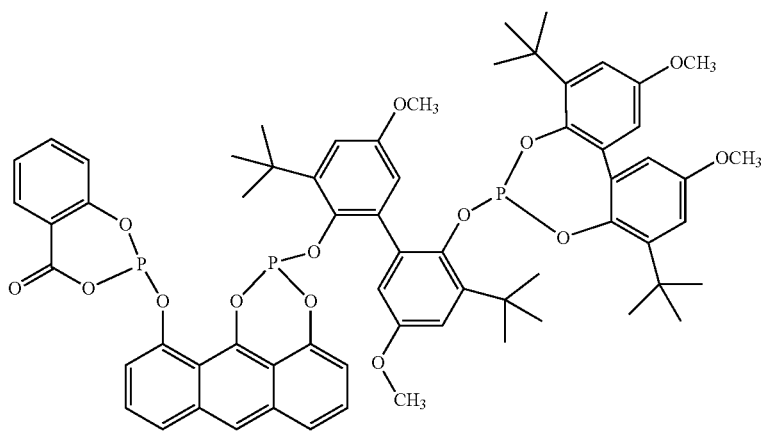
16
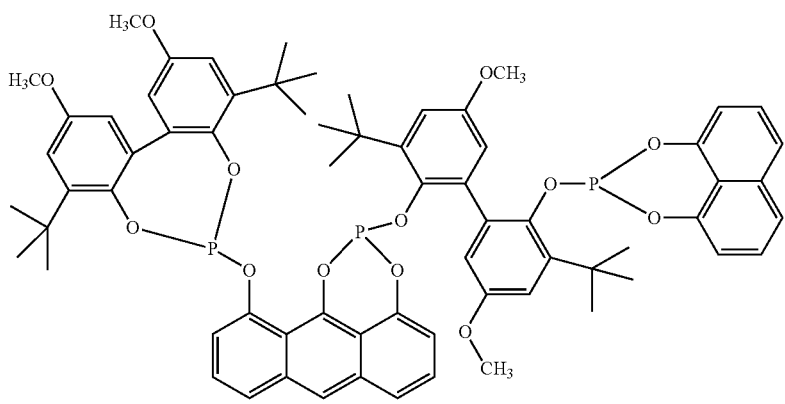
17
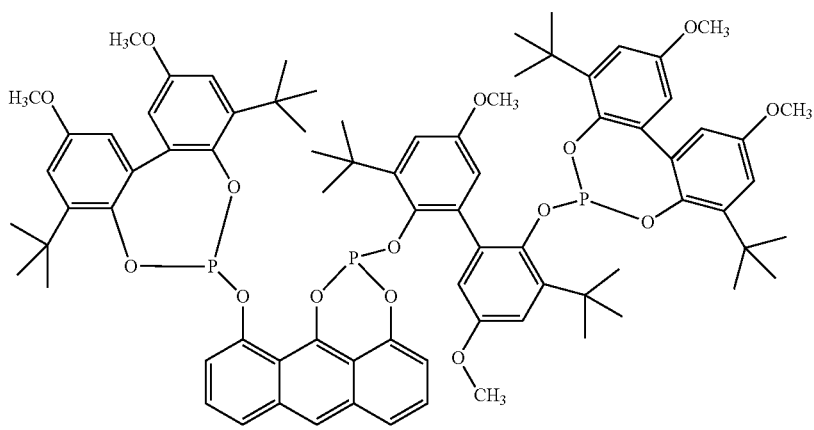
18

Illustrative embodiments of quatrodentate compounds according to the present invention with four phosphorous atoms:

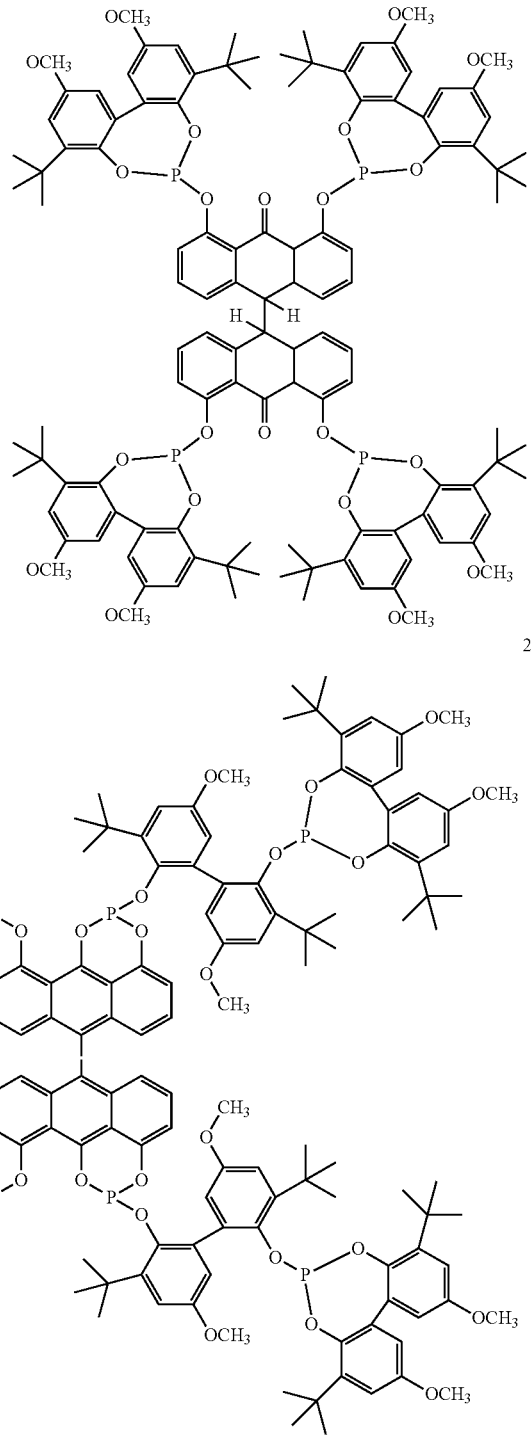

19

20

Synthesis Protocols of Selected Compounds

Compound 1

A suspension of 1,8,9-anthracenetriol (0.3549 g, 1.5686 mmol) in toluene (6 ml) is admixed at 0° C., under agitation, with triethylamine (0.69 ml, 4.939 mmol) and then dropwise with a solution of 4,8-di-tert-butyl-6-chloro-2,10-dimethoxydibenzo[d,f][1,3,2]dioxa-phosphepine (1.3267 g, 3.1372 mmol) in toluene (15 ml). The mixture is stirred overnight and filtered and the filtrate is concentrated to dryness in vacuo. The residue is dried at 40° C. at 0.1 KPa for 2 h and purified by column chromatography (mobile phase dichloromethane, $R_f$=0.62). Yield: 1.39 g (1.39 mmol; 89%). Elemental analysis (calc. for $C_{58}H_{64}O_{11}P_2$=999.08 g/mol): C, 70.17 (69.73); H, 6.50 (6.46); P, 6.07 (6.20) %. $^1$H NMR ($CD_2Cl_2$): δ 0.95-1.59 (36H), 3.76-3.88 (8 signals, 12H); 4.68-5.27 (1H); 6.24-8.00 (15H). Diastereomer ratio=1:5. CI-MS: (isobutane, pos.) m/e 1055 (18%, $M^+$+i-$C_4H_8$), 999 (63%, $M^+$).

Compound 2

A suspension of 1,8,9-anthracenetriol (1.076 g, 4.755 mmol) in toluene (18 ml) is admixed at 0° C. under agitation with triethylamine (2.09 ml, 14.973 mmol) and then dropwise with a solution of 2,4,8,10-tetra-tert-butyl-6-chlorodibenzo [d,f][1,3,2]dioxaphosphepine (4.518 g, 9.511 mmol) in toluene (45 ml). The mixture is stirred overnight at room temperature and for an additional 2 h at 70° C., filtered and the filtrate is concentrated to dryness in vacuo. The residue is prepurified by column chromatography (mobile phase/hexane/dichloromethane=1:2, $R_f$=0.72) and gives a crude yield of 4.27 g (3.869 mmol, 81%). Pure material is obtained by recrystallization of hot acetonitrile. Elemental analysis (calc. for $C_{70}H_{88}O_7P_2$=1103.41 g/mol): C, 76.00 (76.20); H, 7.86 (8.04); P, 5.41 (5.61) %. $^1$H NMR ($CD_2Cl_2$): δ 0.80-1.45 (72H), 4.62-5.13 (1H), 5.69-7.84 (15H) ppm. CI-MS (isobutane, pos.: m/e 1103 (100%, $M^+$).

Compound 3

A suspension of anthracenetriol (0.629 g, 2.782 mmol) in toluene (14 ml) is admixed at 0° C. under agitation with triethylamine (0.866 g, 8.76 mmol) and then dropwise with a solution of 4,8-di-tert-butyl-2,6,10-trichlorodibenzo[d,f][1, 3,2]dioxaphosphepine (2.611 g, 5.563 mmol) in toluene (26 ml). The mixture is stirred overnight and filtered and the filtrate is concentrated to dryness in vacuo. Recrystallization of hexane (65 ml) gives an enriched product (about 85%), which was used for further synthesis. Yield: 1.479 g (1.455 mmol; 52%). $^{31}$P NMR ($CD_2Cl_2$): δ 102.8 (s, br), 105.5 (s, br), 136.5 (s, br), 138.3 (s, br) ppm.

Compound 4

Under agitation, a solution of 1,8,9-anthracenetriol (0.207 g, 0.928 mmol) and triethylamine (0.294 g, 2.92 mmol) in toluene (10 ml) is admixed at −20° C. with a solution of compound 24 (0.882 g, 0.928 mmol) in toluene (10 ml) which is added dropwise. After stirring overnight at room temperature, the reaction solution is filtered and the filtrate is concentrated to dryness in vacuo. The solid material obtained is dried at 50° C./0.1 KPa for 2 h and recrystallized from acetonitrile (100 ml). Yield: 0.391 g (0.411 mmol, 44%). Elemental analysis (calc. for $C_{70}H_{88}O_7P_2$=1103.40 g/mol): C, 75.16 (76.20); H, 8.25 (8.04); P, 5.43 (5.61) %. $^{31}$P NMR ($CD_2Cl_2$): δ □ 102.8 (s, br), 109.8 (s, br), 142.2 (s, br), 142.7 (d, $J_{PP}$=6 Hz) ppm. By NMR spectroscopy there are two diastereomeric products. EI-MS: m/e 1102 (5%, $M^+$).

Compound 5

A solution of 1,8,9-anthracenetriol (0.538 g; 2.378 mmol) and triethylamine (0.757 g, 7.49 mmol) in toluene (20 ml) is admixed at −20° C. under agitation with a solution of 21 (2.011 g, 2.378 mmol) in toluene (30 ml) which is added dropwise. After stirring overnight at room temperature, the reaction solution is filtered and the filtrate is concentrated to dryness in vacuo. The solid material obtained is dried at 50° C./0.1 KPa for 2 h and purified using column chromatography (eluent: dichloromethane, $R_f$=0.46 and 0.51, two diastereoisomers). Yield: 1.263 g (1.264 mmol; 53%). Elemental analysis (calc. for $C_{58}H_{64}O_{11}P_2$=999.08 g/mol): C, 68.96 (69.73); H, 6.28 (6.46); P, 6.17 (6.20) %. $^{31}$P NMR ($CD_2Cl_2$): δ 104.3 (d, $J_{PP}$=37 Hz); 108.5 (d, $J_{PP}$=37 Hz), 138.4 (s, br); 140.5 (s, br) ppm. EI-MS: m/e 998 (2%, M$^+$).

Compound 6

A solution of 5 (0.994 g, 0.995 mmol) in THF (7 ml) is admixed with hexamethyldisilazane (0.802 g, 4.98 mmol), dissolved in THF (12 ml). The reaction solution is refluxed for 10 h and then concentrated to dryness in vacuo. The solid material obtained is dried at 50° C./0.1 KPa for 2 h. The residue is recrystallized from hexane. Yield: 0.877 g (0.819 mmol, 82%). $^1$H NMR ($CD_2Cl_2$): δ 0.15-1.31 (45H), 3.62-3.81 (12H), 6.17-7.94 (m, 15H) ppm.

Compound 7

A solution of 1 (0.966 g, 0.967 mmol) in toluene (12 ml) is admixed at room temperature under agitation with triethylamine (0.42 ml, 3.035 mmol) and then at 0° C. with a solution of 2-chloro-4H-benzo[d][1,3,2]dioxaphosphinin-4-one (0.196 g, 0.967 mmol) in toluene (4 ml). The reaction mixture is warmed to room temperature, stirred overnight and filtered. The filtrate is concentrated to dryness in vacuo, and the residue is dried at 40° C./0.1 KPa for 3 h and then purified by column chromatography (mobile phase hexane/dichloromethane, 1:10, $R_f$=0.8). Yield: 1.095 g (0.939 mmol, 97%). Elemental analysis (calc. for $C_{65}H_{67}O_{14}P_3$=1165.15 g/mol): C, 67.50 (67.01); H, 5.80 (5.80); P, 8.04 (7.97) %. $^1$H NMR ($CD_2Cl_2$): δ 1.08-1.65 (36H), 3.68-3.94 (12H), 6.10-8.10 (19H) ppm. ESI-TOF HRMS (MeOH/0.1% HCOOH in $H_2O$ 90:10) m/e 1187.3633 (100%, M+Na)$^+$.

Compound 8

A solution of 1 (2.0 g, 2.002 mmol) in toluene (20 ml) is admixed at room temperature under agitation with triethylamine (0.88 ml, 6.314 mmol) and then at 0° C. with a solution of 2-chloro-4H-naphtho[1,2-d][1,3,2]dioxaphosphinin-4-one (0.656 mg, 2.602 mmol) in toluene (7 ml). The reaction mixture is warmed to room temperature, stirred overnight and filtered. The filtrate is concentrated to dryness in vacuo, and the residue is dried at 50° C./0.1 KPa for 1 h and then purified by column chromatography (mobile phase hexane/dichloromethane, 1:10, $R_f$=0.62). Yield: 2.07 g (1.703 mmol, 85%). Elemental analysis (calc. for $C_{69}H_{69}O_{14}P_3$=1215.21 g/mol): C, 68.05 (68.20); H, 5.85 (5.72); P, 7.27 (7.65) %. $^1$H NMR ($CD_2Cl_2$): δ 1.09-1.65 (36H), 3.66-3.96 (12H), 6.11-8.24 (21H) ppm. CI-MS (isobutane, pos.): m/e 1214 (1%, M$^+$), 1044.

Compound 9

A solution of 2 (1.329 g, 1.204 mmol) in toluene (15 ml) is admixed at room temperature under agitation with triethylamine (0.53 ml, 3.781 mmol) and then at 0° C. with a solution of 2-chloro-4H-benzo[d][1,3,2]dioxaphosphinin-4-one (0.243 mg, 1.204 mmol) in toluene (5 ml). The reaction mixture is warmed to room temperature, stirred for 48 h and filtered. The filtrate is concentrated to dryness in vacuo, and the residue is dried at 50° C./0.1 KPa for 1 h and then purified by column chromatography (mobile phase hexane/dichloromethane, 2:1, $R_f$=0.22). Yield: 1.14 g (0.898 mmol, 74%). Elemental analysis (calc. for $C_{77}H_{91}O_{10}P_3$=1269.48 g/mol): C, 73.07 (72.85); H, 7.25 (7.23); P, 7.37 (7.32) %. $^{31}$P NMR ($CD_2Cl_2$): δ 102.5-103.7 (1P), 118.5-119.8 (1P), 135.6-136.3 (1P) ppm. EI-MS: m/e 1268 (38%, M$^+$–H), 1085 (43%).

Compound 10 a) Chlorophosphite from 2-hydroxynicotinic acid, 2-chloro-4H-[1,3,2]dioxaphosphinino[4,5-b]pyridin-4-one

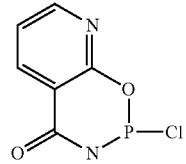 [SMILES: O=C1NP(Cl)Oc2ncccc21]

A solution of 2-hydroxynicotinic acid (0.5 g, 3.594 mmol) and triethylamine (1.5 ml, 10.783 mmol) in THF (20 ml) is admixed under agitation with PCl3 (0.494 g, 3.594 mmol), dissolved in THF (8 ml) and added at −20° C. After stirring at room temperature overnight and at 70° C. for 2 h, the reaction solution is filtered and the solid material is washed with THF (5 ml). The filtrate is concentrated to dryness in vacuo and the yellow residue is dried at 50° C./0.1 KPa for 1 h. Yield: 0.519 g (2.550 mmol, 71%). The solid material has an NMR purity of 95 mol % and was used in the next step of the synthesis without further purification.

$^1$H NMR ($CD_2Cl_2$): δ 7.37 (dd, 1H), 8.40 (dd, 1H), 8.53 (dd, 1H) ppm.

b) Conversion to Compound 10

A solution of 1 (1.859 g, 1.861 mmol) in toluene (22 ml) is admixed at room temperature under agitation with triethylamine (0.82 ml, 5.869 mmol) and then at 0° C. with a solution of 2-chloro-4H-[1,3,2]dioxaphosphinino[4,5-b]pyridin-4-one (0.4544 g, 2.233 mmol) in toluene (14 ml). The mixture is warmed to room temperature, stirred overnight and filtered and the filter cake is washed with THF (2×4 ml). The combined filtrates are concentrated to dryness in vacuo and dried at 50° C./1 mbar for 3 h. The residue is stirred with 50 ml of hexane overnight. After filtering, the solvent is distilled off in vacuo and the solid substance obtained is dried at 70° C./0.1 KPa for 5 h. Yield: 2.00 g (1.715 mmol, 92%). Elemental analysis (calc. for $C_{64}H_{66}O_{14}NP_3$=1166.14 g/mol): C, 64.48 (65.92); H, 5.70 (5.70); P, 7.98 (7.97); N, 1.36 (1.20); $^1$H NMR ($CD_2Cl_2$): δ 0.77-1.62 (36H), 3.56-3.74 (12H), 5.89-8.44 (18H) ppm. EI-MS: m/e 1165 (13%, M$^+$).

Compound 11

A solution of 22 (2.135 g, 1.941 mmol) in toluene (18 ml) is admixed at room temperature under agitation with triethylamine (1.08 ml, 7.765 mmol) and then at 0° C. with solid 1,8,9-anthracenetriol (0.439 g, 1.941 mmol). The mixture is warmed to room temperature, stirred overnight and filtered, the solvent is removed in vacuo, and the residue is dried at 50° C./0.1 KPa for 5 h. Yield: 2.35 g (1.875 mmol, 96%). Elemental analysis (calc. for $C_{72}H_{71}O_{14}P_3$=1253.26 g/mol): C, 69.18 (69.00); H, 5.86 (5.71); P, 7.34 (7.42) %. $^1$H NMR ($CD_2Cl_2$): δ 0.77-1.46 (36H), 3.41-3.71 (12H); 5.78-8.42 (22H), 12.06+12.76 (1H) ppm. EI-MS: m/e 1253 (2%, M$^+$), 999 (100%).

Compound 12

A solution of 22 (1.082 g, 0.983 mmol) in toluene (10 ml) is admixed at room temperature under agitation with triethylamine (0.55 ml, 3.934 mmol) and then at 0° C. with solid 1,9-anthracenediol (0.207 g, 0.983 mmol). The mixture is warmed to room temperature, stirred overnight and filtered, the solvent is removed in vacuo, and the residue is dried at 60° C./0.1 KPa for 4 h. The residue is purified by column chromatography (dichloromethane/hexane=1:1, $R_f$=0.27). Yield: 0.931 g (0.752 mmol, 76%). Elemental analysis (calc. for $C_{72}H_{71}O_{13}P_3$=1237.26 g/mol): C, 69.77 (69.90); H, 5.93 (5.78); P, 7.52 (7.51) %. □$^1$H NMR (CD$_2$Cl$_2$): δ 0.90-1.65 □(36H), 3.61-3.91 (12H), 6.05-8.28 (23H) ppm. EI-MS: m/e 1238 (11%, M$^+$), 982 (43%), 579 (100%).

Compound 13

A solution of 11 (0.674 g, 0.537 mmol) in THF (4 ml) is admixed with a solution of hexamethyldisilazane (0.433 g, 2.689 mmol) in THF (8 ml) added dropwise, refluxed for 14 h and then concentrated to dryness. The residue is purified by column chromatography (eluent hexane/dichloromethane, 1:2, $R_f$=0.47). Yield: 0.482 g (0.364 mmol, 68%). Elemental analysis (calc. for $C_{75}H_{79}O_{14}P_3Si$=1325.44 g/mol): C, 67.59 (67.96); H, 6.09 (6.01); P, 6.89 (7.01); Si, 2.15 (2.12) %. $^1$H NMR (CD$_2$Cl$_2$): δ 0.00-1.53 (45H), 3.20-3.75 (12H), 5.88-7.91 (22H) ppm. According to NMR spectroscopy, there are two diastereomeric products. ESI/TOF-HRMS: m/e 1325.45076 (M+H)$^+$.

Compound 14

A solution of 23 (0.47 g, 0.390 mmol) and triethylamine (0.158 g, 1.561 mmol) in toluene (5 ml) is admixed at 0° C. with solid 1,8,9-anthracenetriol (0.088 g, 0.390 mmol). After stirring at room temperature overnight and at 70° C. for 2 h, the reaction solution is filtered and the filtrate is concentrated to dryness in vacuo. The residue is purified by column chromatography (eluent hexane/dichloromethane, 2:1, $R_f$=0.4). Yield: 0.270 g (0.199 mmol, 51%). Elemental analysis (calc. for $C_{84}H_{95}O_{10}P_3$=1357.58 g/mol): C, 74.30 (74.32); H, 6.89 (7.05); P, 6.80 (6.85) %. $^{31}$P NMR (CD$_2$Cl$_2$): δ 103.2 (s, br), 104.2 (s, br), 104.4 (d, $J_{PP}$=10 Hz), 104.7 (s, br), 105.3 (s), 106.4 (d, $J_{PP}$=10 Hz), 135.6 (s, br), 136.0 (s, br), 136.3 (s, br) ppm. According to NMR spectroscopy, there are three diastereomeric products. ESI/TOF-HRMS: m/e 1357.62109 (M+H)$^+$.

Compound 15

A solution of 3 (1.479 g, 1.455 mmol) and triethylamine (0.462 g, 4.568 mmol) in toluene (20 ml) is admixed under agitation with a solution of 2-chloro-4H-benzo[d][1,3,2]dioxaphosphinin-4-one (0.338 g, 1.673 mmol) in toluene (10 ml) at 0° C. After stirring at room temperature overnight, the reaction solution is filtered and the filtrate is concentrated to dryness in vacuo. The solid material obtained is dried at 50° C./0.1 KPa for 2 h and purified by recrystallizing from acetonitrile. Yield: 1.133 g (0.958 mmol, 66%). Elemental analysis (calc. for $C_{61}H_{55}O_{10}P_3Cl_4$=1182.82 g/mol): C, 61.49 (61.94); H, 4.71 (4.69); P, 7.85 (7.86) %. $^1$H NMR (CD$_2$Cl$_2$): δ 0.82-1.46 (36H), 5.98-7.94 (19 H$_{arom}$). According to NMR spectroscopy, there are six diastereomeric products. EI-MS: m/e 1182 (10%, M$^+$).

Compound 16

A solution of 5 (0.999 g, 1 mmol) in toluene (12 ml) is admixed at room temperature under agitation with triethylamine (0.53 ml, 3.781 mmol) and then at 0° C. with a solution of 2-chloro-4H-benzo[d][1,3,2]dioxaphosphinin-4-one (0.203 g, 1 mmol) in toluene (4 ml). The reaction mixture is warmed to room temperature, stirred overnight and filtered. The filtrate is concentrated to dryness in vacuo, and the residue is dried at 40° C./0.1 KPa for 3 h and then purified by column chromatography (mobile phase hexane/dichloromethane, 1:10, $R_f$=0.8). Yield: 1.107 g (0.950 mmol, 95%) Elemental analysis (calc. for $C_{65}H_{67}O_{14}P_3$=1165.15 g/mol): C, 67.35 (67.01); H, 5.80 (5.80); P, 8.01 (7.97) %. ESI-TOF HRMS (MeOH/0.1% HCOOH in H$_2$O 90:10) m/e 1187.3633 (100%, M+Na)$^+$.

Compound 17

To a solution of 1 (1.487 g, 1.489 mmol) and triethylamine (0.472 g, 4.673 mmol) in toluene (17 ml) is added at 0° C. a solution of 2-chloronaphtho[1,8-de][1,3,2]dioxaphosphinine (0.333 g, 1.489 mmol) in toluene (10 ml). After stirring at room temperature overnight, the reaction solution is filtered and the filtrate is concentrated to dryness in vacuo. The solid material obtained is dried at 50° C./0.1 KPa for 2 h and recrystallized from acetonitrile (20 ml). Yield: 1.087 g (0.915 mmol, 61%). Elemental analysis (calc. for $C_{68}H_{69}O_{13}P_3$=1187.20 g/mol): C, 68.67 (68.80); H, 5.90 (5.86); P, 7.83 (7.83) %. $^1$H NMR (CD$_2$Cl$_2$): δ 1.00-1.63 (36H), 3.67-3.89 (12H), 6.02-8.02 (21H) ppm. EI-MS: m/e 1187 (20%, M$^+$).

Compound 18

A solution of 1 (1.289 g, 1.289 mmol) in THF (12 ml) is admixed at −20° C. with an equimolar amount of n-BuLi in hexane (5 ml). Warming to room temperature is followed by stirring overnight and the mixture thus obtained is added at 0° C. to a solution of 4,8-di-tert-butyl-6-chloro-2,10-dimethoxydibenzo[d, f][1,3,2]dioxa-phosphepine (0.545 g, 1.289 mmol) in THF (9 ml). The mixture is stirred at room temperature for 16 h and concentrated to dryness in vacuo. The residue is stirred with toluene (12 ml) and filtered, the filtrate is concentrated in vacuo and the residue is dried at 50° C./0.1 KPa for 3 h. $^{31}$P NMR (CD$_2$Cl$_2$): δ 102.8, 104.4, 106.6, 109.6, 132.8, 134.4, 134.9, 136.9, 143.4 ppm.

Compound 19 a) Dimeric anthracenetriol by the method of: W. Geiger, Chem. Ber. 1974, 107, 2976-2984.

b) A suspension of anthracenetriol dimer (0.298 g, 0.6615 mmol) in toluene (2 ml) is admixed under agitation with triethylamine (0.29 ml, 2.083 mmol) and then at 0° C. with a solution of 4,8-di-tert-butyl-6-chloro-2,10-dimethoxydibenzo[d,f][1,3,2]dioxaphosphepine (1.119 g, 2.646 mmol) in toluene (10 ml), which is added dropwise. The mixture is stirred at room temperature overnight and at 70° C. for an additional 6 h and filtered, the frit residue is washed with warm toluene (5 ml) and the filtrates are concentrated to dryness in vacuo. Crude yield: 0.589 g (0.295 mmol, 44%). Stirring with acetonitrile (10 ml), filtration, taking up of the frit residue in THF (5 ml) and addition of acetonitrile (8 ml) are followed by crystallization. The solid material obtained is dried in vacuo. Elemental analysis (calc. for $C_{116}H_{126}O_{22}P_4$=1996.15 g/mol): C, 69.48 (69.80); H, 6.20 (6.36); P, 6.15 (6.21) %. $^1$H NMR (CD$_2$Cl$_2$): δ □ 1.35 (36H), 1.37 (36H), 3.37 (2H), 3.66 (12H), 3.71 (12H), 5.60-6.93 (28H) ppm. ESI/TOF-HRMS: m/e 1995.7740 (M$^+$), EI-MS: m/e 998 (47%, homolysis product under excitation conditions of EI-MS).

Compound 20 (2× toluene)

A suspension of anthracenetriol dimer (0.400 g, 0.888 mmol) in toluene (28 ml) is admixed under agitation with triethylamine (0.4 ml, 2.892 mmol) and then at −20° C. with a solution of 21, 4,8-di-tert-butyl-6-(3,3'-di-tert-butyl-2'-(dichlorophosphinooxy)-5,5'-dimethoxybiphenyl-2-yloxy)-

2,10-dimethoxydibenzo[d,f][1,3,2]dioxaphosphepine, (1.488 g, 1.776 mmol) in toluene (32 ml), added dropwise. The mixture is stirred at room temperature overnight and at 70° C. for an additional 2 h and filtered, the filtrate is concentrated to dryness in vacuo and the residue is dried at 50° C./0.1 KPa for 2.5 h. The solid material obtained is stirred with acetonitrile (40 ml) overnight and filtered and the filter residue is dried at 50° C./0.1 KPa for 4 h. Yield: 0.757 g (0.379 mmol, 43%). Elemental analysis (calc. for $C_{130}H_{142}O_{22}P_4$=2180.28 g/mol): C, 70.91 (71.61); H, 6.37 (6.56); P, 5.56 (5.68) %. $^1$H NMR (CD$_2$Cl$_2$): δ □0.74-1.45 (72H), 3.6-3.7 (24H), 6.2-9.1 (28H), 11.56-12.13 (2H) ppm. ESI/TOF-HRMS: m/e 1996.7820 (M+H toluene$_2$)$^+$ Compound 21

4,8-Di-tert-butyl-6-(3,3'-di-tert-butyl-2'-(dichlorophosphinooxy)-5,5'-dimethoxybiphenyl-2-yloxy)-2,10-dimethoxy-dibenzo[d,f][1,3,2]dioxaphosphepine A solution of 3,3'-di-tert-butyl-2'-(4,8-di-tert-butyl-2,10-dimethoxydibenzo[d,f][1,3,2]dioxaphosphepin-6-yloxy)-5,5'-dimethoxybiphenyl-2-ol (prepared by the method of D. Selent, D. Hess, K.-D. Wiese, D. Röttger, C. Kunze, A. Börner, Angew. Chem. 2001, 113, 1739) (11.37 g, 15.26 mmol) and triethylamine (3.09 g, 30.54 mmol) in toluene (133 ml) is admixed under agitation with PCl$_3$ (2.51 g, 18.31 mmol), dissolved in toluene (17 ml), at 0° C. After stirring at room temperature overnight and at 85° C. for 3.5 h, the reaction solution is filtered and the filtrate is concentrated to dryness in vacuo. The residue is dried at 60° C./1 mbar for 2.5 h, then dissolved in hexane (125 ml) and stored at 5° C. overnight. The crystalline material obtained is filtered, and the filtrate residue is washed with cold hexane (20 ml) and dried. Yield: 8.97 g (10.6 mmol, 69%). $^1$H NMR (CD$_2$Cl$_2$): δ□ 1.17 (s, 9H), 1.30 (s, 9H), 1.51 (s, 9H), 1.56 (s, 9H), 3.81 (s, 3H), 3.85 (2 s, 6H), 3.86 (3H), 6.71 (d, 1H), 6.74 (d, 1H), 6.81 (d, 1H), 6.83 (d, 1H), 6.95 (d, 1H), 7.04 (d, 1H), 7.06 (d, 1H), 7.09 (d, 1H) ppm. EI-MS, m/e 809 (2%, [M−Cl]$^+$); 727 (100%).

Compound 22

A solution of 1 (1.0 g, 1.001 mmol) in toluene (6 ml) is admixed at room temperature under agitation with triethylamine (0.28 ml, 2.002 mmol) and then at 0° C. with a solution of phosphorus trichloride (0.152 g, 1.1 mmol) in toluene (2 ml). After warming to room temperature, stirring overnight and filtration, the solvent is removed in vacuo. The residue is stirred with 10 ml of hexane for 16 h and filtered, the filter residue is dried at 50° C./0.1 KPa for 3 h. Yield: 0.86 g (0.781 mmol, 78%). $^{31}$P NMR (CD$_2$Cl$_2$): δ 102.8 (s), 103.5 (s), 103.9 (d), 134.9 (s, br), 198.7 (s), 199.3 (s), 203.3 (d) ppm (diastereomer mixture). The summed intensities in the particular expectation range correspond to a 1:1:1 ratio for the 3 P atoms.

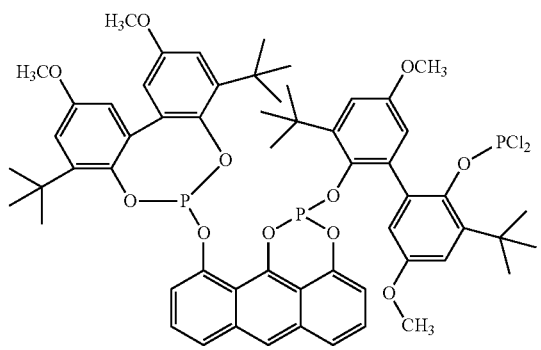

22

Compound 23

A solution of 2 (0.6 g, 0.545 mmol) and triethylamine (0.109 g, 1.087 mmol) in toluene (9 ml) was admixed under agitation with a solution of PCl3 (0.070 g, 0.516 mmol) in toluene (2 ml) added dropwise at 0° C. After stirring at room temperature overnight, the reaction solution is filtered and the filtrate is concentrated to dryness in vacuo. The residue is dried at 50° C./0.1 KPa for 3 h and used in the next step of the synthesis without further purification. $^{31}$P NMR (CD$_2$Cl$_2$): δ□100.9 (dd, J$_{PP}$=71 Hz; 4 Hz), 102.9 (s, br), 103.4 (dd, J$_{PP}$=3 Hz; 3 Hz), 135.2 (s, br), 135.7 (dd, J$_{PP}$=8 Hz, 4 Hz), 135.9 (s, br), 199.9 (dd, J$_{PP}$=71 Hz, 8 Hz), 203.1 (d, J$_{PP}$=3 Hz), 203.2 (s, br).

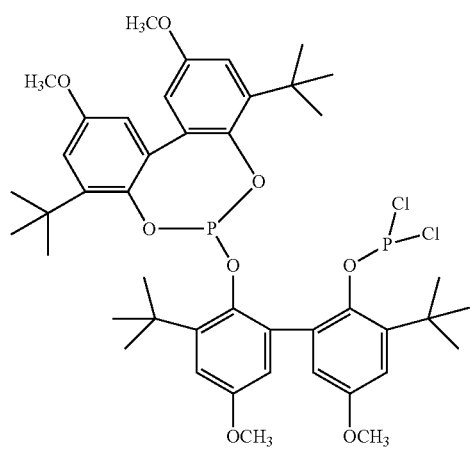

21

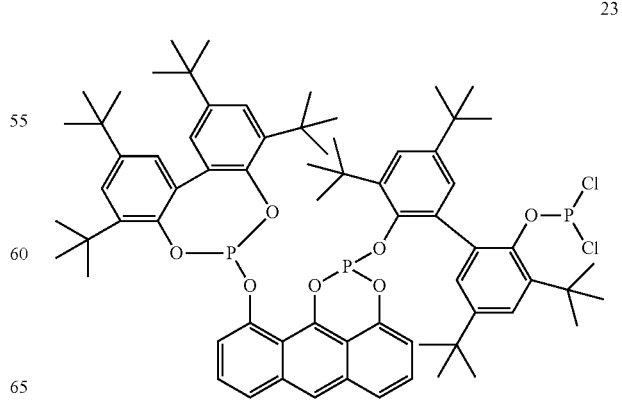

23

Compound 24

Compound 24 was prepared similarly to 21 by reacting the corresponding phosphite phenol (D. Selent, D. Hess, K.-D. Wiese, D. Röttger, C. Kunze, A. Börner, *Angew. Chem.* 2001, 113, 1739) with PCl$_3$. The crude product was washed with hexane and dried at 50° C./0.1 KPa for 2 h to obtain spectroscopically pure material. Yield: 72%. $^1$H NMR (CD$_2$Cl$_2$): δ 1.11 (s, 9H), 1.27 (s, 9H), 1.36 (s, 9H), 1.38 (s, 9H), 1.40 (s, 9H), 1.41 (s, 9H), 1.52 (s, 9H), 1.58 (s, 9H), 7.14 (d, J$_{HH}$=2.5 Hz, 1H), 7.16 (d, J$_{HH}$=2.5 Hz, 1H), 7.24 (d, J$_{HH}$=2.5 Hz, 1H), 7.31 (d, J$_{HH}$=2.5 Hz, 1H), 7.39 (d, J$_{HH}$=2.5 Hz, 1H), 7.50 (d, J$_{HH}$=2.5 Hz, 1H), 7.53 (d, J$_{HH}$=2.5 Hz, 1H), 7.55 (d, J$_{HH}$=2.5 Hz, 1H) ppm.

24

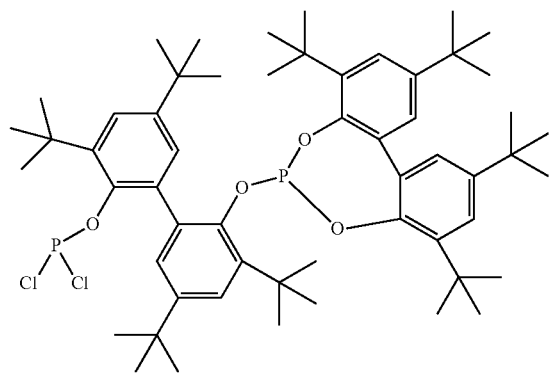

NMR-Spectroscopic Testing for Stability

Ligand 17 and the bidentate comparative ligand BiPhePhos were each dissolved in untreated toluene-D$_8$, transferred into an NMR vial and sealed. The ligand content was tracked by NMR spectroscopy for 32 days.

Figure 1B:
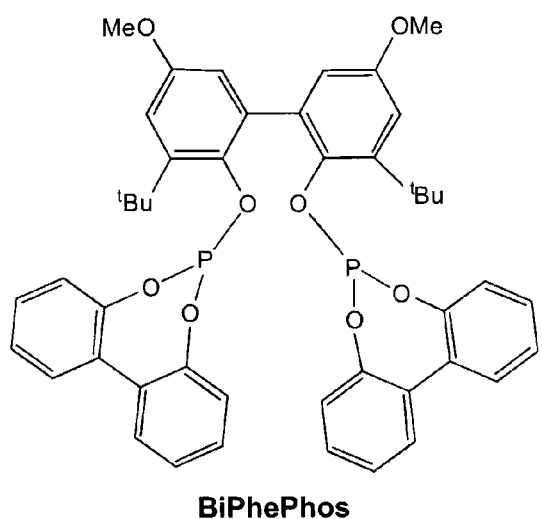
FIG. 1B shows the chemical structure of comparative ligand BiPhePhos.

The results are shown in FIG. 1. Ligand 17 has a significantly higher stability than the comparative ligand BiPhePhos, as is clearly apparent in FIG. 1. In fact, the comparative ligand BiPhePhos is no longer NMR-detectable after day 32, while ligand 17 is measured at a concentration of 60% relative to the initial value.

From this stability test of free ligand 17 and of free BiPhePhos ligand, the stability of a corresponding catalytically active composition, as of the rhodium complex derivatives formed therefrom for example, is directly derivable. For a hydroformylation process operated with this catalytically active composition, it means that the on-stream time of a catalytically active composition based on ligand 17 is distinctly extended and thus economically optimized. This is accomplished without need for a further stabilizing component, for example the addition of sterically bulky amine derivatives—disclosed in EP 2280920. The subsequent catalyst tests with different olefins or different olefin-containing hydrocarbonaceous streams demonstrate this technical teaching in detail.

Verification Structure of Tridentate Character

A rhodium complex of ligand 17 was prepared and isolated in x-ray suitable quality. The structure derived from the x-rayograph is as follows:

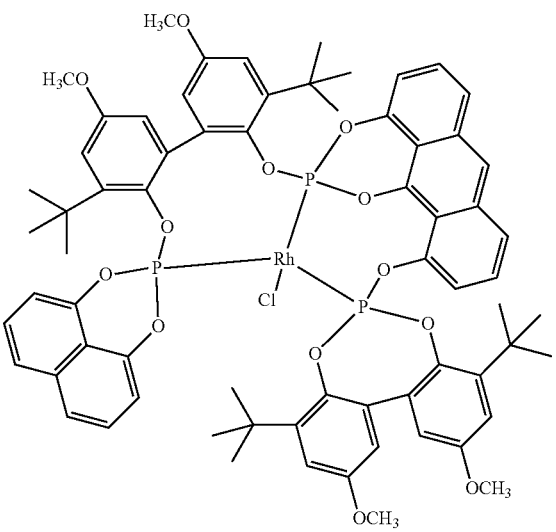

The data obtained verify the 3-fold coordination of rhodium on P$^{III}$. Hence the solution contains a potentially higher P$^{III}$ concentration on the transition metal with the consequence that:

rhodium is kept in solution, and thus in the form of the catalytically active composition, better and the literature-described clustering of rhodium is suppressed.

Ligand dissociation and clustering are less favoured than in bidentate systems, thus providing the catalytically active composition with a longer on-stream time.

Verification Structure of Tridentate Character as Binuclear Structure

A rhodium complex of ligand 17 was prepared and isolated in x-ray suitable quality. The structure derived from the x-rayograph is as follows:

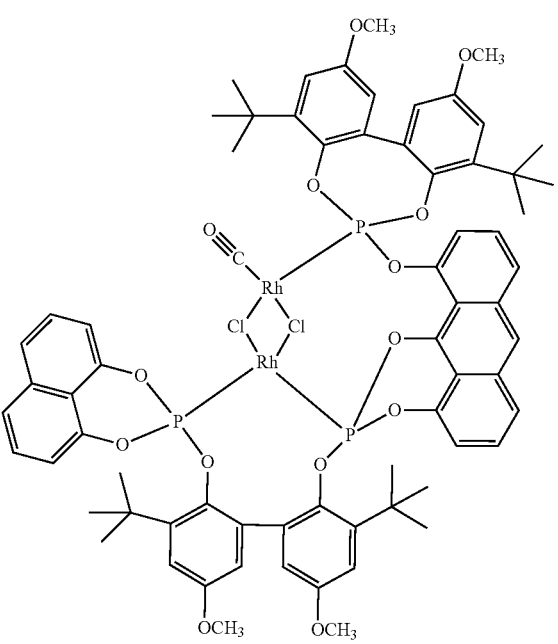

The data obtained additionally verify the structure of a binuclear rhodium complex in the catalytically active composition. The stabilization of a second rhodium atom per complex in the catalytically active composition is thus proven and thereby additionally prevents any clustering, i.e. loss of rhodium.

Of the initially outlined requirements for novel ligands, the 5 points:
improved resistance to inherent catalyst poisons and also suppression of rhodium clustering by multiple coordination with tridentate ligands and forming binuclear complexes are satisfied by providing the compounds of the present invention and by their use as ligands.

The ability of compounds according to the present invention to effect isomerizing hydroformylation when used as ligands in a catalytically active composition is disclosed in the following catalysis tests on olefins and also olefin-containing mixtures:

Operating Prescription for Catalysis Tests

The hydroformylation was carried out in a 200 ml autoclave equipped with a pressure regulator to keep a constant pressure, a gas flowmeter, a sparging stirrer and a pressure pipette. To minimize any influence due to moisture and oxygen, not only the solvents (Tol=toluene, PC=propylene carbonate, THF=tetrahydrofuran) but also the substrates were dried. For the tests, the autoclave was filled under argon with solutions of rhodium in the form of [(acac)Rh(COD)] (acac=acetylacetonate anion; COD=1,5-cyclooctadiene) as catalyst precursor in toluene. Then, the corresponding amount of toluene-dissolved phosphite compound, generally from 2 to 5 ligand equivalents per rhodium, was admixed. The mass of toluene introduced in each case was determined. Starting weight of olefins: 1-octene (10.62 g, 94.64 mmol), n-octene (10.70 g, 95.35 mmol), 2-pentene (2.81 g, 40.0 mmol, characterized in table below with "(P)", or 9.75 g, 139.00 mmol. 1-Butene, 2-butene and isobutene were added in similar fashion. The autoclave was heated to the particular reported temperatures at an overall gas pressure (synthesis gas: $H_2$ (99.999%): $CO_2$ (99.997%)=1:1) of a) 4.2 MPa for a final pressure of 5.0 MPa; b) 1.2 MPa for the final pressure of 2.0 MPa; and c) 0.7 MPa for a final pressure of 1.0 MPa; under agitation (1500 rpm). On reaching the reaction temperature, the synthesis gas pressure was raised to a) 4.85 MPa for a final pressure of 5.0 MPa, b) 1.95 MPa for a final pressure of 2.0 MPa and c) 0.95 MPa for a final pressure of 1.0 MPa and the particular olefin or olefin-containing mixture reported in the table was injected at about 0.3 MPa overpressure setting in the pressure pipette. The reaction was carried on for 4 h at a constant pressure of respectively 5.0, 2.0 and 1.0 MPa. After the reaction time had passed, the autoclave was cooled down to room temperature, let down under agitation and purged with argon. A 1 ml sample of each reaction mixture was taken immediately the stirrer was switched off, diluted with 5 ml of pentane and analyzed by gas chromatography: HP 5890 Series II plus, PONA, 50 m×0.2 mm×0.5 µm. Quantitative determination of aldehyde and residual olefin was against the solvent toluene as internal standard.

Catalysis tests with compounds 6 to 17.

Yield=yield based on starting olefin or olefin-containing mixture

Sel. (%)=n-selectivity (%)

1-Octene

| Ligand | P (MPa) | T (° C.) | t (h) | [Rh] (ppm) | L/Rh | Solvent | Yield (%) | Sel. (%) |
|---|---|---|---|---|---|---|---|---|
| 7 | 5.0 | 100 | 4 | 40 | 1 | Tol | 85 | 95.8 |
| 7 | 5.0 | 100 | 4 | 40 | 2 | Tol | 86 | 95.5 |
| 9 | 5.0 | 100 | 4 | 40 | 2 | Tol | 86 | 94.9 |
| 9 | 5.0 | 100 | 4 | 40 | 2 | PC | 84 | 95.0 |
| 10 | 5.0 | 100 | 4 | 40 | 2 | Tol | 87 | 95.6 |
| 15 | 5.0 | 100 | 4 | 40 | 2 | Tol | 86 | 96.1 |
| 11 | 5.0 | 100 | 4 | 40 | 2 | Tol | 90 | 97.2 |
| 16 | 5.0 | 100 | 4 | 40 | 2 | Tol | 90 | 91.0 |
| 17 | 5.0 | 100 | 4 | 40 | 4 | Tol | 91 | 89.5 |

All ligands used are tridentate and perform in the reaction with good to outstanding yields and also respectively outstanding n-selectivities. The respective catalytically active compositions need only minimal ligand excesses for these performances, as the L/Rh ratio in the table shows.

n-Octenes (octene isomer mixture of 1-octene: 3.3%, cis+trans-2-octene: 48.5%, cis+trans-3-octene: 29.2%, cis+trans-4-octene: 16.4%, structurally isomeric octenes: 2.6%)

| Ligand | P (MPa) | T (° C.) | t (h) | [Rh] (ppm) | L/Rh | Solvent | Yield (%) | Sel. (%) |
|---|---|---|---|---|---|---|---|---|
| 7 | 2.0 | 120 | 4 | 100 | 1 | Tol | 68 | 84.2 |
| 7 | 2.0 | 120 | 4 | 100 | 2 | Tol | 79 | 85.5 |
| 7 | 2.0 | 120 | 4 | 100 | 10 | Tol | 74 | 85.6 |
| 8 | 2.0 | 120 | 4 | 100 | 2 | PC | 85 | 87.1 |
| 17 | 2.0 | 120 | 4 | 100 | 2 | Tol | 76 | 84.4 |

All ligands used are tridentate and perform in the reaction with good to outstanding yields and also respectively outstanding n-selectivities. The respective catalytically active compositions need only minimal ligand excesses for these performances, as the L/Rh ratio in the table shows. Higher ligand excesses are unnecessary, as is illuminated by the example of ligand 7 in the table.

2-Pentene (15 ml, 2.41 M)

(P) characterizes lower 2-pentene use (see above)

| Ligand | P (MPa) | T (° C.) | t (h) | [Rh] (ppm) | L/Rh | Solvent | Yield (%) | Sel. (%) |
|---|---|---|---|---|---|---|---|---|
| 7 | 2.0 | 120 | 4 | 100 | 1 | Tol (P) | 93 | 89.6 |
| 7 | 2.0 | 120 | 4 | 100 | 1 | PC (P) | 87 | 91.6 |
| 7 | 2.0 | 120 | 4 | 100 | 2 | Tol (P) | 95 | 90.2 |
| 7 | 2.0 | 120 | 4 | 100 | 2 | PC (P) | 93 | 92.4 |
| 7 | 2.0 | 120 | 4 | 100 | 2 | PC | 90 | 92.2 |
| 7 | 2.0 | 120 | 4 | 100 | 5 | Tol | 95 | 90.0 |
| 7 | 2.0 | 120 | 4 | 100 | 10 | Tol (P) | 95 | 90.4 |
| 7 | 2.0 | 120 | 4 | 100 | 2 | Tol | 94 | 89.7 |
| 7 | 2.0 | 120 | 4 | 120 | 1.7 | Tol | 96 | 89.9 |
| 7 | 2.0 | 120 | 4 | 100 | 2/2 TINUVIN® | Tol | 96 | 90.2 |
| 7 | 2.0 | 100 | 4 | 100 | 2 | PC | 89 | 91.7 |
| 7 | 2.0 | 100 | 4 | 100 | 2 | Tol | 91 | 90.5 |
| 7 | 2.0 | 120 | 4 | 100 | 2 | Tol | 94 | 89.7 |
| 8 | 2.0 | 120 | 4 | 100 | 2 | PC | 95 | 92.7 |
| 8 | 2.0 | 120 | 4 | 100 | 5 | PC | 92 | 92.6 |
| 8 | 2.0 | 120 | 4 | 100 | 10 | PC | 95 | 92.6 |
| 8 | 2.0 | 120 | 4 | 100 | 2 | Tol | 95 | 90.6 |
| 8 | 2.0 | 120 | 4 | 100 | 2 | THF | 94 | 91.0 |
| 8 | 1.0 | 120 | 4 | 100 | 2 | PC | 92 | 90.7 |
| 8 | 2.0 | 100 | 4 | 100 | 2 | PC | 93 | 92.0 |
| 8 | 2.0 | 110 | 4 | 100 | 2 | PC | 94 | 92.4 |

-continued

| Ligand | P (MPa) | T (°C.) | t (h) | [Rh] (ppm) | L/Rh | Solvent | Yield (%) | Sel. (%) |
|---|---|---|---|---|---|---|---|---|
| 10 | 2.0 | 120 | 4 | 100 | 2 | PC | 92 | 92.6 |
| 10 | 2.0 | 120 | 4 | 100 | 2 | Tol | 95 | 90.2 |
| 10 | 2.0 | 120 | 4 | 100 | 5 | Tol | 95 | 90.2 |
| 10 | 2.0 | 100 | 4 | 100 | 2 | PC | 90 | 92.8 |
| 11 | 2.0 | 120 | 4 | 100 | 2 | Tol | 95 | 93.8 (P) |
| 11 | 2.0 | 120 | 4 | 100 | 2 | Tol | 96 | 93.9 |
| 11 | 2.0 | 120 | 4 | 100 | 2 | PC | 93 | 94.3 (P) |
| 11 | 2.0 | 120 | 4 | 100 | 1 | Tol | 91 | 93.4 (P) |
| 11 | 2.0 | 120 | 4 | 100 | 5 | Tol | 95 | 94.4 (P) |
| 11 | 1.0 | 120 | 4 | 100 | 2 | Tol | 96 | 93.6 |
| 11 | 1.0 | 110 | 4 | 100 | 2 | Tol | 91 | 94.1 |
| 11 | 2.0 | 120 | 4 | 100 | 2 | PC | 99 | 94.4 |
| 11 | 1.0 | 110 | 4 | 100 | 2 | PC | 94 | 95.1 |
| 11 | 1.0 | 100 | 4 | 100 | 2 | PC | 90 | 95.8 |
| 11 | 2.0 | 100 | 4 | 100 | 2 | PC | 87 | 93.9 |
| 12 | 2.0 | 120 | 4 | 100 | 2 | Tol | 97 | 90.4 |
| 12 | 2.0 | 120 | 4 | 100 | 2 | PC | 97 | 91.9 |
| 12 | 1.0 | 100 | 4 | 100 | 2 | PC | 87 | 94.2 |
| 13 | 2.0 | 120 | 4 | 100 | 2 | PC | 89 | 94.5 |
| 13 | 1.0 | 110 | 4 | 100 | 2 | PC | 84 | 95.6 |
| 13 | 1.0 | 110 | 4 | 100 | 2 | PC | 91 | 95.4 |
| 14 | 2.0 | 120 | 4 | 100 | 2 | Tol | 88 | 89.7 (P) |
| 15 | 2.0 | 120 | 4 | 100 | 2 | PC | 95 | 92.6 |
| 15 | 2.0 | 120 | 4 | 100 | 2 | Tol | 91 | 90.1 |
| 6 | 2.0 | 120 | 4 | 100 | 2 | Tol | 65 | 88.6 |
| 17 | 2.0 | 100 | 4 | 100 | 2 | Tol | 87 | 89.6 |
| 17 | 2.0 | 120 | 4 | 100 | 2 | Tol | 93 | 90.8 |
| 17 | 2.0 | 120 | 4 | 100 | 5 | Tol | 97 | 90.2 |
| 17 | 2.0 | 120 | 4 | 100 | 2 | PC | 97 | 91.8 |

The extensive series of catalysis tests with 2-pentene has 2 special features compared with the other series of tests:

a bidentate compound is used in ligand 6 and a distinct reduction in yield compared with the other ligands used is recorded;

the tridentate ligand 7 is reacted in one test together with a sterically bulky amine derivative branded as TINUVIN®=di-4-(2,2,6,6-tetramethyl)piperidinyl sebacate—without better results being achieved in respect of yield and n-selectivity.

C4 Olefins

| Ligand | Substrate | P (MPa) | T (°C.) | t (h) | [Rh] (ppm) | L/Rh | Solvent | Yield (%) | Sel. (%) |
|---|---|---|---|---|---|---|---|---|---|
| 17 | 2-Butene | 2.0 | 120 | 5 | 40 | 3.9 | Toluene | 93.8 | 90.2 |
| 17 | 1-Butene | 2.0 | 120 | 5 | 37 | 6.0 | Toluene | 82.2 | 87.8 |
| 17 | Isobutene | 2.0 | 100 | 5 | 38 | 6.0 | Toluene | 64.6 | 100 |

The invention claimed is:

1. A compound comprising:

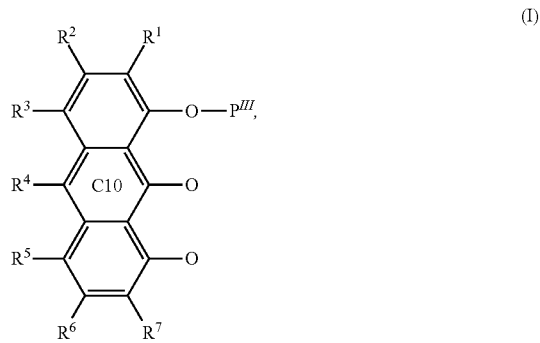

wherein $R^1, R^2, R^3, R^4, R^5, R^6$, and $R^7$ are selected from the group consisting of hydrogen, a substituted or unsubstituted, linear or branched, aliphatic or aromatic hydrocarbon group; F, Cl, Br, I, $-OR^8$, $-C(O)R^9$, $-CO_2R^{10}$, $-CO_2M^1$, $-SR^{11}$, $-SOR^{12}$, $-SO_2R^{13}$, $-SO_3R^{14}$, $-SO_3M^2$, $-NR^{15}R^{16}$; and $-OR^{17}$, where $R^8, R^9, R^{10}, R^{11}, R^{12}, R^{13}, R^{14}, R^{15}, R^{16}$ are independently hydrogen, a substituted or unsubstituted, linear or branched, aliphatic or aromatic or heteroaromatic or fused aromatic or fused aromatic-heteroaromatic hydrocarbon group; and $R^{17}$ is hydrogen, an unsubstituted or substituted, linear or branched, aliphatic or an aromatic hydrocarbon group; and $M^1$ and $M^2$ are each independently selected from the group consisting of an alkali metal, an alkaline earth metal, ammonium, and phosphonium;

wherein when said compound comprises two structures of formula (I), then the two structures are connected at the $R^4$ (C10) positions via a carbon-carbon bond between the $R^4$ (C10) positions on each structure or via:

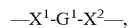

where $X^1$ is connected to a $P^{III}$ of the first structure and $X^2$ to a $P^{III}$ of the second structure, wherein $P^{III}$ is a phosphorous atom having a valence of 3, $G^1$ is a linear or branched, aliphatic or aromatic or heteroaromatic or fused aromatic or fused aromatic-heteroaromatic hydrocarbon group with any desired further substitution, $X^1$, and $X^2$ are each independently selected from the group consisting of O, $NY^1$, and $CY^2Y^3$, where $Y^1$, $Y^2$, and $Y^3$ are each independently selected from the group consisting of hydrogen, a substituted or unsubstituted aliphatic group, and a substituted or unsubstituted aromatic hydrocarbon group, wherein, optionally, two or more of $Y^1$ to $Y^3$ are covalently-linked to each other;

wherein, optionally, two or more of $R^1$ to $R^{17}$ are covalently-linked to each other;

wherein said compound comprises at least two $O-P^{III}$ bonds which may be formed between oxygen atoms and the same or separate P atom(s).

2. The compound according to claim 1, comprising a structure of formula (II):

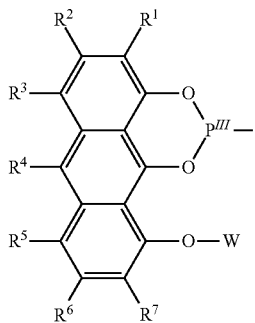

(II)

wherein W is selected from the group consisting of:
hydrogen
an optionally substituted aliphatic, aromatic, heteroaromatic, fused aromatic, or fused aromatic-heteroaromatic hydrocarbon group;
a $P^{III}(G^2)(G^3)$ group:

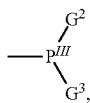

where
$G^2$ and $G^3$ are each independently selected from the group consisting of hydrogen; an optionally substituted linear or branched, aliphatic or aromatic or heteroaromatic or fused aromatic or fused aromatic-heteroaromatic hydrocarbon group; F, Cl, Br, I, —$OR^{18}$, —$C(O)R^{19}$, —$CO_2R^{20}$, —$CO_2M^1$, —$SR^{21}$, —$SOR^{22}$, —$SO_2R^{23}$, —$SO_3R^{24}$, —$SO_3M^2$, —$NR^{25}R^{26}$; and —$OR^{27}$, where $R^{18}$, $R^{19}$, $R^{20}$, $R^{21}$, $R^{22}$, $R^{23}$, $R^{24}$, $R^{25}$, and $R^{26}$ are selected from the group consisting of hydrogen, a substituted or unsubstituted, linear or branched, aliphatic or aromatic hydrocarbon group, $R^{27}$ is selected from the group consisting of hydrogen, a substituted or unsubstituted, linear or branched, aliphatic or aromatic hydrocarbon group; F, Cl, Br, and I; and $M^1$ and $M^2$ are each independently selected from the group consisting of an alkali metal, an alkaline earth metal, ammonium, and phosphonium, and $G^2$ and $G^3$ are optionally linked to each other covalently; and $SiR^{28}R^{29}R^{30}$, where $R^{28}$, $R^{29}$, $R^{30}$ are each independently hydrogen; or an optionally substituted linear or branched, aliphatic or aromatic or heteroaromatic or fused aromatic or fused aromatic-heteroaromatic hydrocarbon group where $R^{28}$ and $R^{29}$ are optionally covalently linked to each other.

3. The compound according to claim 2, comprising a structure of formula (III):

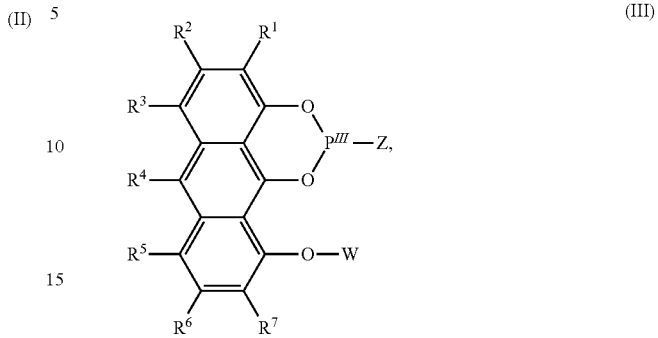

(III)

wherein
Z is $G^4$ or an $X^1$-$G^1$-$X^2$ unit,
where $G^4$ is selected from the group consisting of hydrogen; and an optionally substituted linear or branched, aliphatic or aromatic or heteroaromatic or fused aromatic or fused aromatic-heteroaromatic hydrocarbon group, F, Cl, Br, I, —$OR^{31}$, —$C(O)R^{32}$, —$CO_2R^{33}$, —$CO_2M^1$, —$SR^{34}$, —$SOR^{35}$, —$SO_2R^{36}$, —$SO_3R^{37}$, —$SO_3M^2$, —$NR^{38}R^{39}$, and —$OR^{40}$;
where $R^{31}$, $R^{32}$, $R^{33}$, $R^{34}$, $R^{35}$, $R^{36}$, $R^{37}$, $R^{38}$, $R^{39}$, and $R^{40}$ are selected from the group consisting of hydrogen, and a substituted or unsubstituted, linear or branched, aliphatic or aromatic hydrocarbon group; and
$M^1$ and $M^2$ are each independently selected from the group consisting of an alkali metal, an alkaline earth metal, ammonium, and phosphonium.

4. The compound according to claim 2, comprising a structure of formula (IV):

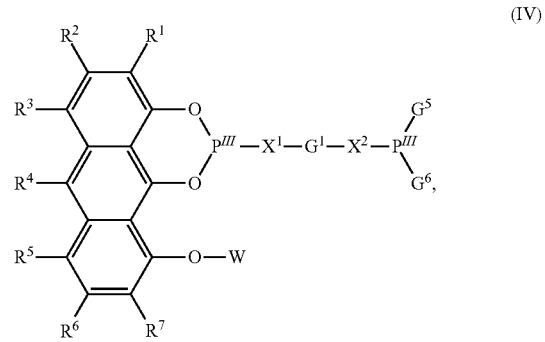

(IV)

wherein $G^5$ and $G^6$ are each independently selected from the group consisting of hydrogen; an optionally substituted linear or branched, aliphatic or aromatic or heteroaromatic or fused aromatic or fused aromatic-heteroaromatic hydrocarbon group; F, Cl, Br, I, —$OR^{41}$, —$C(O)R^{42}$, —$CO_2R^{43}$, —$CO_2M^1$, —$SR^{44}$, —$SOR^{45}$, —$SO_2R^{46}$, —$SO_3R^{47}$, —$SO_3M^2$, —$NR^{48}R^{49}$; and —$OR^{50}$;
where $R^{41}$, $R^{42}$, $R^{43}$, $R^{44}$, $R^{45}$, $R^{46}$, $R^{47}$, $R^{48}$, $R^{49}$, and $R^{50}$ are selected from the group consisting of hydrogen, and a substituted or unsubstituted, linear or branched, aliphatic or aromatic hydrocarbon group; and
$M^1$ and $M^2$ are each independently selected from the group consisting of an alkali metal, an alkaline earth metal, ammonium, and phosphonium, and
$G^5$ and $G^6$ are optionally covalently linked to each other.

5. The compound according to claim 2,
wherein W is a $P^{III}(G^2)(G^3)$ group.
6. The compound according to claim 2,
wherein $G^2$, and $G^3$ are $-OR^{18}$.
7. The compound according to claim 4,
wherein $G^5$, and $G^6$ are $-OR^{41}$.
8. The compound according to claim 1,
wherein $X^1$, and $X^2$ are O.
9. The compound according to claim 1,
wherein $G^1$ comprises an optionally substituted bisarylene group.
10. The compound according to claim 1,
wherein $G^1$ comprises a structure of formula (V):

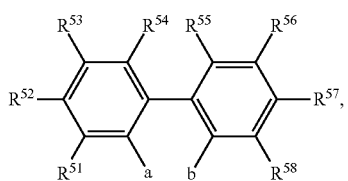

(V)

where
$R^{51}$, $R^{52}$, $R^{53}$, $R^{54}$, $R^{55}$, $R^{56}$, $R^{57}$, and $R^{58}$ are each independently hydrogen; an optionally substituted linear or branched, aliphatic or aromatic or heteroaromatic or fused aromatic or fused aromatic-heteroaromatic hydrocarbon group; F, Cl, Br, I; $-OR^{59}$, $-COR^{60}$, $-CO_2R^{61}$, $-CO_2M^1$, $-SR^{62}$, $-SOR^{63}$, $-SO_2R^{64}$, $-SO_3R^{65}$, $-SO_3M^2$, $-NR^{66}R^{67}$; or $-OR^{68}$,
two or more of $R^{51}$ to $R^{58}$ are optionally covalently linked to each other;
$R^{59}$, $R^{60}$, $R^{61}$, $R^{62}$, $R^{63}$, $R^{64}$, $R^{65}$, $R^{66}$, $R^{67}$ and $R^{68}$ are selected from the group consisting of hydrogen, and substituted or unsubstituted, linear or branched, aliphatic or aromatic hydrocarbon group;
$M^1$ and $M^2$ are each independently selected from the group consisting of an alkali metal, an alkaline earth metal, ammonium, and phosphonium, and
a and b are attachment points to $X^1$ and $X^2$.
11. The compound according to claim 2,
wherein $G^2$ and $G^3$ are covalently linked to each other.
12. The compound according to claim 2,
wherein $G^2$-$G^3$ comprises a structure of formula (VI):

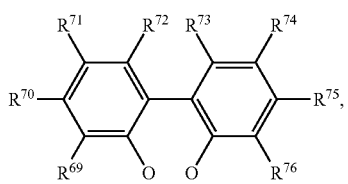

(VI)

where $R^{69}$, $R^{70}$, $R^{71}$, $R^{72}$, $R^{73}$, $R^{74}$, $R^{75}$, and $R^{76}$ are each independently hydrogen; an optionally substituted linear or branched, aliphatic or aromatic or heteroaromatic or fused aromatic or fused aromatic-heteroaromatic hydrocarbon group; F, Cl, Br, I; $-OR^{77}$, $-COR^{78}$, $-CO_2R^{79}$, $-CO_2M^1$, $-SR^{80}$, $-SOR^{81}$, $-SO_2R^{82}$, $-SO_3R^{83}$, $-SO_3M^2$, $-NR^{84}R^{85}$; or $-OR^{86}$,
two or more of $R^{69}$ to $R^{76}$ are optionally covalently linked;
$R^{77}$, $R^{78}$, $R^{79}$, $R^{80}$, $R^{81}$, $R^{82}$, $R^{83}$, $R^{84}$, $R^{85}$ and $R^{86}$ are selected from the group consisting of hydrogen, and a substituted or unsubstituted, linear or branched, aliphatic or aromatic hydrocarbon group; and
$M^1$ and $M^2$ are each independently selected from the group consisting of an alkali metal, an alkaline earth metal, ammonium, and phosphonium.
13. The compound according to claim 4,
wherein $G^5$ and $G^6$ are covalently linked to each other.
14. The compound according to claim 4,
wherein $G^5$-$G^6$ comprises a structure of formula (VII):

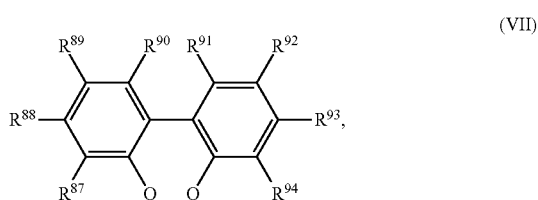

(VII)

where $R^{87}$, $R^{88}$, $R^{89}$, $R^{90}$, $R^{91}$, $R^{92}$, $R^{93}$, and $R^{94}$ are each independently hydrogen; an optionally substituted linear or branched, aliphatic or aromatic or heteroaromatic or fused aromatic or fused aromatic-heteroaromatic hydrocarbon group; F, Cl, Br, I; $-OR^{95}$, $-COR^{96}$, $-CO_2R^{97}$, $-CO_2M^1$, $-SR^{98}$, $-SOR^{99}$, $-SO_2R^{100}$, $-SO_3R^{101}$, $-SO_3M^2$, $-NR^{102}R^{103}$; or $-OR^{104}$,
two or more of $R^{87}$ to $R^{94}$ are optionally covalently linked to each other covalently;
$R^{95}$, $R^{96}$, $R^{97}$, $R^{98}$, $R^{99}$, $R^{100}$, $R^{101}$, $R^{102}$, $R^{103}$ and $R^{104}$ are selected from the group consisting of hydrogen, and a substituted or unsubstituted, linear or branched, aliphatic or aromatic hydrocarbon group; and
$M^1$ and $M^2$ are each independently selected from the group consisting of an alkali metal, an alkaline earth metal, ammonium, and phosphonium.
15. The compound according to claim 4,
wherein the $P^{III}(G^2)(G^3)$ group corresponds in terms of structural formula to the $P^{III}(G^5)(G^6)$ group.
16. A complex, comprising:
the compound according to claim 1, and
a central metal atom,
wherein the compound is coordinated onto the central metal atom via at least one $P^{III}$.
17. The complex according to claim 16,
wherein the central metal atom is one of groups 8 to 10 metals.
18. The complex according to claim 17, wherein the central metal atom is rhodium.
19. A composition, comprising:
a central metal atom, and
at least two compounds according to claim 1,
wherein
a first compound is not coordinated onto a central metal atom, and
a second compound is coordinated onto the central metal atom via at least one $P^{III}$.
20. A multiphasic reaction mixture, comprising:
an olefinically unsaturated hydrocarbon mixture,
a gas mixture comprising carbon monoxide and hydrogen, aldehydes, and
the composition according to claim 19 as a catalytically active composition.
21. A process for hydroformylation of an olefinically unsaturated hydrocarbon mixture to aldehydes, comprising:
adding the catalytically active composition according to claim 19 into the mixture;

introducing a mixture comprising carbon monoxide and hydrogen, thereby obtaining a reaction mixture;

heating the reaction mixture to a temperature of from 80 to 120° C.;

building a pressure of from 1.0 to 6.4 MPa; and removing the olefinically unsaturated hydrocarbon mixture.

22. The process according to claim 21, further comprising recycling unconverted olefinically unsaturated hydrocarbon mixture.

23. The process according to claim 21, further comprising removing and recycling the catalytically active composition.

24. The process according to claim 21, further comprising removing and recycling unconverted gas mixture comprising carbon monoxide and hydrogen.

* * * * *